United States Patent
Wu et al.

(10) Patent No.: US 11,497,799 B2
(45) Date of Patent: Nov. 15, 2022

(54) DICKKOPF2 (DKK2) INHIBITION SUPPRESSES TUMOR FORMATION

(71) Applicant: YALE UNIVERSITY, New Haven, CT (US)

(72) Inventors: Dianqing Wu, Cheshire, CT (US); Le Sun, Beijing (CN)

(73) Assignee: YALE UNIVERSITY, New Haven, CT (US)

( * ) Notice: Subject to any disclaimer, the term of this patent is extended or adjusted under 35 U.S.C. 154(b) by 576 days.

(21) Appl. No.: 16/529,174

(22) Filed: Aug. 1, 2019

(65) Prior Publication Data

US 2020/0093903 A1    Mar. 26, 2020

Related U.S. Application Data

(62) Division of application No. 15/322,595, filed as application No. PCT/US2015/038581 on Jun. 30, 2015, now Pat. No. 10,398,765.

(60) Provisional application No. 62/020,684, filed on Jul. 3, 2014.

(51) Int. Cl.

| G01N 33/574 | (2006.01) |
|---|---|
| A61K 39/00 | (2006.01) |
| C07K 16/18 | (2006.01) |
| A61P 35/04 | (2006.01) |
| A61K 39/395 | (2006.01) |
| C07K 16/28 | (2006.01) |

(52) U.S. Cl.
CPC ........ *A61K 39/0011* (2013.01); *A61K 39/395* (2013.01); *A61P 35/04* (2018.01); *C07K 16/18* (2013.01); *C07K 16/2818* (2013.01); *G01N 33/574* (2013.01); *G01N 33/57496* (2013.01); *A61K 2039/505* (2013.01); *A61K 2039/507* (2013.01); *C07K 2317/76* (2013.01); *G01N 2800/52* (2013.01)

(58) Field of Classification Search
CPC ........... G01N 33/574; G01N 33/57496; G01N 2800/52
See application file for complete search history.

(56) References Cited

U.S. PATENT DOCUMENTS

| 2005/0261181 A1 | 11/2005 | Wu et al. |
| 2006/0204496 A1 | 9/2006 | Kojima et al. |
| 2009/0311253 A1 | 12/2009 | Ghayur et al. |
| 2010/0104577 A1 | 4/2010 | Golde et al. |
| 2012/0023600 A1 | 1/2012 | Shulok et al. |
| 2013/0309250 A1 | 11/2013 | Cogswell et al. |

FOREIGN PATENT DOCUMENTS

| WO | 0006714 A1 | 2/2000 |
| WO | 2007084344 A2 | 7/2007 |
| WO | 2007122815 A1 | 11/2007 |
| WO | 2009149185 A2 | 12/2009 |
| WO | 2009149189 A2 | 12/2009 |

OTHER PUBLICATIONS

Extended European Search Report for European Patent Application No. 15816061.4 dated Apr. 10, 2018.
International Search Report and Written Opinion for PCT International Application No. PCT/US2015/038581 dated Dec. 7, 2015.
Supplementary Partial European Search Report for European Patent Application No. 15816061.4 dated Dec. 18, 2017.
Bahrami, et al., "Therapeutic Potential of Targeting Wnt/β-Catenin Pathway in Treatment of Colorectal Cancer: Rational and Progress", J Cell Biochem. 118(8), 2017, 1979-1983.
Brott, et al., "Regulation of Wnt/LRP signaling by distinct domains of Dickkopf proteins", Mol Cell Biol. 22(17), 2002, 6100-6110.
Hauer, et al., "DKK2 mediates osteolysis, invasiveness, and metastatic spread in Ewing sarcoma", Cancer Res. 73 (2), 2013, 967-977.
Hirano, et al., "Blockade of B7-H1 and PD-1 by monoclonal antibodies potentiates cancer therapeutic immunity", Cancer Res. 65(3), 2005, 1089-1096.
Hirata, et al., "Wnt antagonist gene DKK2 is epigenetically silenced and inhibits renal cancer progression through apoptotic and cell cycle pathways", Clin Cancer Res.15(18), 2009, 5678-5687.
Lau, et al., "A novel tankyrase small-molecule inhibitor suppresses APC mutation-driven colorectal tumor growth", Cancer Res. 73(10), 2013, 3132-3144.
Li, et al., "Chemical and genetic evidence for the involvement of Wnt antagonist Dickkopf2 in regulation of glucose metabolism", Proc Natl Acad Sci U S A. 109(28), 2012, 11402-11407.
Li, et al., "MicroRNA-222 promotes tumorigenesis via targeting DKK2 and activating the Wnt/β-catenin signaling pathway", FEBS Lett. 587(12), 2013, 1742-1748.
Li, et al., "Second cysteine-rich domain of Dickkopf-2 activates canonical Wnt signaling pathway via LRP-6 independently of dishevelled", J Biol Chem. 277(8), 2002, 5977-5981.

(Continued)

*Primary Examiner* — Daniel C Gamett
(74) *Attorney, Agent, or Firm* — Saul Ewing Arnstein & Lehr LLP; Kathryn Doyle; Justin Crotty

(57) ABSTRACT

The present invention relates to the discovery that inhibition of Dickkopf2 (DKK2) increases CD8+ cytotoxic T lymphocyte (CTL) activity, attenuates tumor angiogenesis, and hence suppresses tumor formation. Thus, in various embodiments described herein, the methods of the invention relate to methods of treating cancer by administering to a patient an effective amount of DKK2 gene depleting agent, methods for providing anti-tumor immunity and anti-tumor angiogenesis in a subject, methods of stimulating a T cell mediated immune response to a cell population or a tissue and suppressing tumor angiogenesis in a subject. Additionally, the current invention includes methods of diagnosing a cancer or a predisposition of developing a cancer or a metastasis and methods for determining the use of immunotherapy treatment or cancer vaccine for treating cancer. Furthermore, the invention encompasses a pharmaceutical composition for treating cancer as well as a kit for carrying out the aforementioned methods.

13 Claims, 20 Drawing Sheets

Specification includes a Sequence Listing.

(56) References Cited

OTHER PUBLICATIONS

Min, et al., "The WNT antagonist Dickkopf2 promotes angiogenesis in rodent and human endothelial cells", J Clin Invest. 121(5), 2011, 1882-1893.
Monaghan, et al., "Dickkopf genes are co-ordinately expressed in mesodermal lineages", Mech Dev. 87(1-2), 1999, 45-56.
Niehrs, "Function and biological roles of the Dickkopf family of Wnt modulators", Oncogene. Dec. 4, 2006;25(57), 2006, 7469-7481.
Niida, et al., "DKK1, a negative regulator of Wnt signaling, is a target of the beta-catenin/TCF pathway", Oncogene. 23(52), 2004, 8520-8526.
Park, et al., "Distinct roles of DKK1 and DKK2 in tumor angiogenesis", Angiogenesis. 17(1), 2014, 221-234.
Saif, "Anti-VEGF agents in metastatic colorectal cancer (mCRC): are they all alike?", Cancer Manag Res. 5, 2013, 103-115.
Sato, et al., "Frequent epigenetic inactivation of DICKKOPF family genes in human gastrointestinal tumors", Carcinogenesis. 28(12), 2007, 2459-2466.
Song, et al., "Neuroprotective Role of Dickkopf2 (Dkk2) in the endothelial cells after the cerebral ischemia", Society for Neuroscience, Chicago, IL, 2009, Abstract.
Sugimachi, "Dickkopf-2 Variant [Homo Sapiens]", GenBank: BAB20420, 2001, 1.
Wang, et al., "Dickkopf-Related Protein 2 is Epigenetically Inactivated and Suppresses Colorectal Cancer Growth and Tumor Metastasis by Antagonizing Wnt/β-Catenin Signaling", Cell Physiol Biochem. 41(5), 2017, 1709-1724.
Xiao, et al., "DKK2 imparts tumor immunity evasion through β-catenin-independent suppression of cytotoxic immune-cell activation", Nat Med. 24(3), 2018, 262-270.
Yanagida, et al., "Downregulation of the Wnt antagonist Dkk2 links the loss of Sept4 and myofibroblastic transformation of hepatic stellate cells", Biochim Biophys Acta. 1812(11), 2011, 1403-1411.
Ying, et al., "Epigenetic disruption of the WNT/beta-catenin signaling pathway in human cancers", Epigenetics. 4(5), 2009, 307-312.
You, et al., "Developmental abnormalities in multiple proliferative tissues of Apc(Min/+) mice", Int J Exp Pathol. 87(3), 2006, 227-236.
Zhang, et al., "The LRP5 high-bone-mass G171V mutation disrupts LRP5 interaction with Mesd", Mol Cell Biol. 24(11), 2004, 4677-4684.

APC
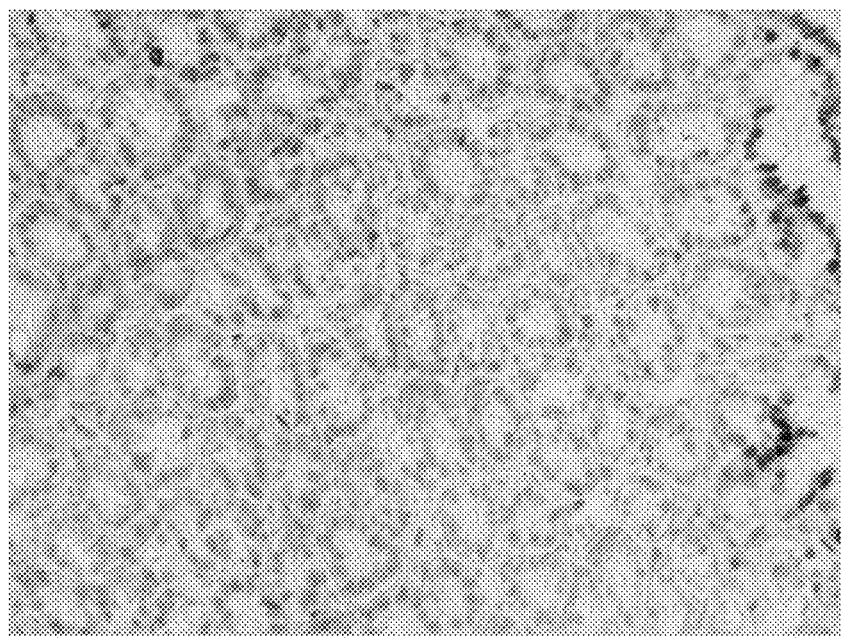
APCKO
FIG. 5

| SEQ ID NO | ID | Amino acid Sequence | Immunogenicity | |
|---|---|---|---|---|
| 1 | YAL008-1* | 34-KLNSIKSSLGGETPGC#-48 | 8.2 | DKK2-specific |
| 2 | YAL008-2 | 148-RDRNHGHYSNHDC#-159 | 23.2 | DKK2-specific |
| 3 | YAL008-3 | 166-GRPHTKMSHIKGC#-177 | 12.2 | DKK2-specific |
| 4 | YAL008-4 | 215-TKQRKKGSHGLEC#-226 | 20 | DKK2- non-specific |
| 5 | YAL008-5** | 239-CKVWKDATYSSKAR-252 | 10.4 | DKK2-specific |
| 6 | YAL008-6 | Met172–Ile259 of mouse Dkk2 | | Recombinant DKK2- C terminal |
| 7 | YAL008-7 | 195-CARHFWTKIC-204 | | |

Antibodies of particular interest:   * 5F8: KLNSIKSSLGGETPGC
                                     ** 1A10: CKVWKDATYSSKAR "#" denotes the Cysteine residue added for conjugation.

Amino acid sequence for SEQ ID NO: 6
MPHIKGHEG DPCLRSSDCI DGFCCARHFW TKICKPVLHQ GEVCTKQRKK GSHGLEIFQR CDCAKGLSCK VWKDATYSSK ARLHVCQKI

YAL008-5 1A10 Heavy Chain peptide sequence (SEQ ID NO: 8):
LQQSGPELVKPGASVKISCKASGYSFTGYFVNWVKQSHGKSLDWIGRIIPYNGDTFYNQKFKG KATLTVDKSSTTAHMELLSLTSEDSAVYYCGRGDYWGQGTSVTVSS

YAL008-5 1A10 Light Chain peptide sequence (SEQ ID NO: 9):
PLTLSVTIGQPASISCKSSQSLLDSDGKTYLNWLLQRPGQSPKRLIYLVSKLDSGVPDRFTGSG SGTDFTLKISRVEAEDLGVYYCWQGTHFPQTFGGGTKLEIK

YAL008-1 5F8 Heavy Chain peptide sequence (SEQ ID NO: 10):
GAELVRPGASVKLSCKASGYSFTNYWMNWVKQRPGQGLEWIGMIHPSDSETRLNQKFKDKA TLTVDKSSSTAYMQLSSPTSEDSAVYYCAREGRLGLRSYAMDYWGQGTSVTVSS

YAL008-1-5F8 Light Chain peptide sequence (SEQ ID NO: 11):
PSSLAMSVGQKVTMSCKSSQSLLNSSNQKNYLAWYQQKPGQSPKLLVYFASTRESGVPDRFV GSGSGTDFTLTITSVQAEDLADYFCQQHYITPLTFGAGTKLE

YAL008-7-1A10 Light Chain peptide sequence (SEQ ID NO: 12):
SNPVTSGESVSISCRSSKSLLYKDGKTYLNWFLQRPGQSPQLLIYLMSTRASGVSDRFSGSGS GTDFTLEISRVKAEDVGVYYCQQLVEYPYTFGGGTKLEI

YAL008-7-1A10 Heavy Chain peptide sequence (SEQ ID NO: 13):
SGAELVKPGASVKMSCKASGYTFTNYWMHWVKQRPGQGLEWIGTIDPSDSYTSYNQKFKGK ATLTVDTSSSTAYMQLSSLTSEDSAVYYCTYYDYDWFAYWGQGTTVTVSS

DICKKOPF2 (DKK2) INHIBITION SUPPRESSES TUMOR FORMATION

CROSS-REFERENCE TO RELATED APPLICATION

The present application is a divisional of, and claims priority to, U.S. patent application Ser. No. 15/322,595, filed Dec. 28, 2016, now U.S. Pat. No. 10,398,765, which is a 35 U.S.C. § 371 national phase application from, and claims priority to, International Application No. PCT/US2015/038581, filed Jun. 30, 2015, and published under PCT Article 21(2) in English, which claims priority under 35 U.S.C. § 119(e) to U.S. Provisional Application No. 62/020,684, filed Jul. 3, 2014, all of which applications are incorporated herein by reference in their entireties.

STATEMENT REGARDING FEDERALLY SPONSORED RESEARCH OR DEVELOPMENT

This invention was made with government support under grant CA132317 awarded by National Institute of Health. The government has certain rights in the invention.

BACKGROUND OF THE INVENTION

Cancer is a major health problem worldwide. Each year, tens of millions of people are diagnosed with cancer around the world, and more than half of the patients eventually die from it. About one-half of all men and one-third of all women in the US will be diagnosed with a cancer at some point during their lifetime, and one in four deaths is caused by cancer (Jemal et al., CA Cancer J. Clin., 2002, 52:23-47; Howlader et al., SEER Cancer Statistics Review, 1975-2010, National Cancer Institute). The most-commonly identified human cancers include those that arise from organs and solid tissues, e.g., colon cancer, lung cancer, breast cancer, stomach cancer, prostate cancer, and endometrial cancer. Colon cancer affects 1 in 20 people in the western hemispheres (Henderson, Nature Cell Biology, 2000, 2(9): p. 653-60). Globally, every year 1 million new patients are diagnosed with colon cancer and half of them succumb to this disease (Liu et al., Cell, 2002, 108(6): p. 837-47).

In the past decades remarkable advancements in cancer treatment and diagnosis have occurred. Treatment options for cancer includes surgery, chemotherapy, radiation therapy, and immunotherapy. Most recently immunotherapy treatment, aiming on stimulating the immune system, has particularly attracted lots of investigations. Although immunotherapy could be highly efficacious, only small subsets of patients regardless of the organ of origin of the tumor are usually responsive to therapy. New findings in this field are clearly needed for improving immunotherapy efficacy and specificity.

Wnt-signaling controls a wide variety of cell processes, including cell fate determination, differentiation, polarity, proliferation and migration. The Wnt family of secreted proteins bind to several classes of receptors, such as the low-density lipoprotein receptor related (LRP) proteins 5 and -6 (LRP5/6), resulting in activation of several different intracellular signaling cascades, including the Wnt/β-catenin, Wnt/calcium and Wnt/Jnk pathways. Binding of Wnts to LRP5/6 specifically activates the Wnt/β-catenin pathway by blocking the function of a multiprotein complex that primes β-catenin for degradation, resulting in accumulation of β-catenin in the cytoplasm and nucleus. Nuclear β-catenin complexes with members of the Lef/TCF family of transcription factors and activates gene expression.

Pathological states that may arise from altered stem cell function, such as degenerative diseases and cancer, are frequently associated with changes in Wnt/β-catenin pathway activity. Indeed, hyperactivation of the Wnt/β-catenin pathway is thought to induce premature senescence of stem cells and age-related loss of stem cell function (Brack et al., Science, 2007, Vol. 317 no. 5839 pp. 807-810; Liu et al., Science, 2007, Vol. 317 no. 5839 pp. 803-806). In cancer, hyperactivation of the Wnt/β-catenin pathway, often in conjunction with mutations in other cell growth regulatory genes, can lead to aberrant cell growth (Reya and Clevers, Nature, 2005, 434(7035):843-50). Thus, many ongoing investigations are focusing on Wnt/β-catenin pathway as a potential therapeutic target in cancer (Breuhahn et al., Oncogene, 2006, 25: 3787-3800; Greten et al., Br J Cancer, 2009, 100: 19-23). Particularly, several research studies including cancer genomic sequencing projects revealed that more than 80% of colon cancers harbor a mutation or even a loss of the adenomatosis polyposis coli (APC) gene, a major suppressor of the Wnt/β-catenin pathway (Kinzler and Vogelstein, Cell. 1996, Oct. 18; 87(2):159-70. Review; Sjoblom et al., Science, 2006, Oct. 13; 314(5797):268-74; Mann et al., Proc Natl Acad Sci USA, 1999. 96(4): p. 1603-8). APC and proteins such as GSK3β and Axin form a complex which marks β-catenin for degradation. Mutations in APC disrupt this complex and leads to increased levels of cytoplasmic β-catenin and its nuclear translocation. Since β-catenin is the most important adaptor of the Wnt signaling it promotes expression of oncogenic factors in response to Wnt ligands.

Wnt signaling is also regulated by a number of secreted polypeptide antagonists. These include four secreted Dickkopf (Dkk) proteins (Monaghan et al., Mech Dev, 1999. 87: 45-56; Krupnik et al., Gene, 1999. 238: 301-13). Among these four Dkk proteins, DKK1, 2 and 4 have been demonstrated to be effective antagonists of canonical Wnt signaling (Mao et al., Nature, 2001. 411: 321-5; Semenov et al., Curr Biol, 2001. 11: 951-61; Bafico et al., Nat Cell Biol, 2001. 3: 683-6; Niehrs, Nature, 2006. 25: 7469-81) by directly binding to Wnt coreceptor LRP 5/6 with high affinities (Mao et al., Nature, 2001. 411: 321-5; Semenov et al., Curr Biol, 2001. 11: 951-61; Bafico et al., Nat Cell Biol, 2001. 3: 683-6). While DKK1 is reported to play a crucial role in head and heart formation in vertebrate development (Niida et al., Oncogene, 2004, Nov. 4; 23(52):8520-6), Dkk2 does not appear to play cortical roles in vertebrate development. Mice lacking Dkk2 have lower blood glucose (Li et al., Proc Natl Acad Sci USA, 2012. 109: 11402-7), reduced bone mass (Li et al., Nat Genet, 2005. 37: 945-52) and defective ocular surface epithelia (Gage et al., Dev Biol, 2008. 317: 310-24; Mukhopadhyay et al., Development, 2006. 133: 2149-54). Given that DKK proteins are Wnt antagonists, the conventional wisdom is that inactivation of DKK would increase Wnt activity and hence accelerate cancer formation. However, their roles in cancer formation has not been directly investigated.

The Dkk molecules contain two conserved cysteine-rich domains (Niehrs, Nature, 2006. 25: 7469-81). Previously, it was shown that the second Cys-rich domains of DKK1 and DKK2 played a more important role in the inhibition of canonical Wnt signaling (Li et al., J Biol Chem, 2002. 277:5977-81; Brott and Sokol Mol. Cell. Biol., 2002. 22:6100-10). More recently, the structure of the second Cys-rich domain of DKK2 was solved and delineated amino acid residues on the domain that are required for DKK interaction with LRP5/6 and those for Kremens (Chen et al., J Biol Chem, 2008. 283: 23364-70; Wang et al., J Biol Chem, 2008. 283: 23371-5). Dkk interaction with LRP5/6 underlie the primary mechanism for Dkk-mediated inhibition of Wnt. Although Dkk interaction with Kremen, also a transmembrane protein, was shown to facilitate Dkk antagonism of Wnt signaling, this interaction may have other unresolved functions. Ala scan mutagenesis identified amino acid residues on the third YWTD repeat domain of LRP5 as being important for binding to DKK1 and DKK2 (Zhang et al., Mol. Cell. Biol., 2004. 24:4677-84). These results have been confirmed by the structural studies of a DKK1/LRP6 third and fourth YWTD repeat domain complex (Cheng et al., Nat Struct Mol Biol, 2011. 18:1204-10; Chen et al., Dev Cell, 2011. 21: 848-61; Ahn et al., Dev Cell, 2011. 21:862-73.; Bourhis et al., Structure, 2011. 19:1433-42). One of the structural studies also revealed a second DKK-LRP interaction site between the N-terminus of DKK and the first YWTD repeat domain of LRP (Bourhis et al., Structure, 2011. 19: 1433-42).

Although Wnt signaling was initially discovered for its role in early embryonic development and for its promotion of tumorigenesis, recent studies have revealed that is plays important roles in a wide range of biological processes. The present invention derives from unexpected discovery of a role of a Wnt antagonist, against the conventional wisdom, in tumor promotion. The neutralization of this Wnt inhibitor, which would result in alteration of Wnt signaling, inhibits tumor formation probably by modulating the tumor immune microenvironment. Clearly there is a need of new ways to diminish cancer cell proliferation, to trigger cancer cell death, and to treat cancer. The current invention fulfills this need. Furthermore, the present invention satisfies the need for improving anti-cancer immunotherapy and cancer diagnosis.

SUMMARY OF THE INVENTION

The present invention relates to compositions and methods of treating a cancer in a subject in need thereof. The method of treating a cancer comprises administering to the subject an effective amount of a Dickkopf2 (DKK2) gene depleting agent in a pharmaceutical acceptable carrier.

In another aspect, the invention includes a method of treating or reducing angiogenesis in a subject in need thereof. The method comprises administering to the subject an effective amount of a DKK2 gene depleting agent in a pharmaceutical acceptable carrier. In some embodiments, the angiogenesis is a tumor angiogenesis associated with cancer. In other embodiments, the angiogenesis is a pathological angiogenesis associated with ischaemic and inflammatory diseases. In yet other embodiments, the angiogenesis is associated with a cardiovascular disease.

In another aspect, the invention includes a pharmaceutical composition for treating a cancer in a subject. The pharmaceutical composition of the present invention comprises a DKK2 depleting agent and a pharmaceutical acceptable carrier.

In yet another aspect, the invention provides a method for providing anti-tumor immunity in a subject. The method comprises administering to the subject an effective amount of a DKK2 antibody or fragment thereof with a pharmaceutical acceptable carrier. In a further aspect, the invention provides a method for stimulating a T cell-mediated immune response to a cell population or tissue in a subject. The method comprises administering to the subject an effective amount of a DKK2 antibody or fragment thereof with a pharmaceutical acceptable carrier. In some embodiments, the T cell-mediated immune response is a $CD8^+$ cytotoxic T lymphocyte (CTL) response.

The invention also provides a method of diagnosing a cancer or a predisposition for developing a cancer in a subject. The method comprises determining the expression level of a DKK2 gene in a biological sample from the subject, wherein an increase in the expression level of DKK2 in the biological sample from the subject as compared with the level of DKK2 expression in a control biological sample from a subject not having a cancer is an indication that the subject has a cancer or a predisposition for developing a cancer, and wherein when a cancer or a predisposition for developing a cancer is detected in a subject, treatment is recommended for the subject.

The invention further provides a method for determining the efficacy of a treatment for cancer in a subject in need thereof. The method comprises determining the expression level of DKK2 gene in a biological sample from the subject, wherein an increase in the expression level of DKK2 in the biological sample from the subject as compared with the level of DKK2 expression in a control biological sample from a subject not having a cancer is an indication that the treatment is effective, and wherein when the treatment is determined to be effective recommending additional treatment for the subject. In some embodiments, the treatment comprises at least one selected from the group consisting of chemotherapy, radiation therapy, immunotherapy and cancer vaccine therapy.

In a further aspect, the invention includes a composition comprising a neutralizing DKK2 antibody targeting a DKK2 epitope comprising at least one of the amino acid sequences selected from the group consisting of SEQ ID NOs: 1, 5 and 7.

In yet a further aspect, the invention includes a kit for diagnosing a cancer or a predisposition for developing a cancer or a metastasis in a subject. The kit comprises a reagent selected from the group consisting of: a reagent for detecting mRNA of a DKK2 gene, a reagent for detecting a DKK2 protein and a reagent for detecting a biological activity of a DKK2 protein.

In some embodiments, the cancer comprises a tumor comprising cells that express an adenomatosis polyposis coli (APC) mutation. In some embodiments, the DKK2 depleting agent is selected from the group consisting of a DKK2 antibody, siRNA, ribozyme, an antisense molecule, an aptamer, a peptidomimetic, a small molecule, and a combination thereof. In some embodiments, the DKK2 depleting agent possesses neutralizing activity. In other embodiments, the DKK2 antibody comprises an antibody selected from the group comprising a polyclonal antibody, monoclonal antibody, humanized antibody, synthetic antibody, heavy chain antibody, human antibody, biologically active fragment of an antibody, an antibody mimic and any combination thereof. In yet other embodiments, the DKK2 antibody targets a DDK2 neutralizing epitope that comprises at least one of the amino acid sequences selected from the group consisting of SEQ ID NOs: 1, 5 and 7. In further embodiments, the DKK2 antibody is a synthetic antibody comprising at least one of the amino acid sequences selected from the group consisting of YAL008-5-1A10 (SEQ ID NOs 8 and 9), YAL008-7-1A10 (SEQ ID NOs 12 and 13) and YAL008-1-5F8 (SEQ ID NOs 10 and 11).

In some embodiments, the cancer is selected from the group consisting of colorectal cancer, pancreatic cancer, gastric cancer, intestinal cancer, pancreatic cancer, and esophageal cancer. In some embodiments, the cancer is metastatic.

In some embodiments, the compositions and methods of the invention further comprise administering to the subject an additional agent selected from the group consisting of a chemotherapeutic agent, an anti-cell proliferation agent, an immunotherapeutic agent and any combination thereof. In some embodiments, the additional agent is a programmed cell death 1 (PD-1) antibody. In other embodiments, the DKK2 depleting agent and the additional agent are co-administered to the subject. In yet other embodiments, the DKK2 depleting agent and the additional agent are co-formulated and are co-administered to the subject.

In some embodiments, the route of administration is selected from the group consisting of inhalation, oral, rectal, vaginal, parenteral, topical, transdermal, pulmonary, intra-nasal, buccal, ophthalmic, intrathecal, and any combination thereof.

In some embodiments, the expression level of DKK2 gene in the biological sample from the subject is at least 10% greater than the normal control level. In some embodiments, the expression level is determined by a method selected from the group consisting of detecting mRNA of the gene, detecting a protein encoded by the gene, and detecting a biological activity of the protein encoded by the gene.

In some embodiments, the treatment of the present invention comprises of at least a DKK2 depleting agent.

In some embodiments, the subject is a mammal. In other embodiments, the mammal is a human.

In further embodiments, the reagent of the kit of the present invention comprises a neutralizing DKK2 antibody targeting a DKK2 epitope comprising at least one of the amino acid sequences selected from the group consisting of SEQ ID NOs: 1, 5 and 7.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A: Tumor/polyp number. FIG. 1B: Tumor/polyp size: APCKO tumors tend to be smaller than those of APC mice. FIG. 1C: Representative H and E staining reveals smaller and less frequent tumors in APCKO mice.

FIG. 2A: 50K cells were plated. After overnight serum starvation, recombinant (r)DKK2 was added to the medium. 24 hrs later, proliferation was measured using an ATPlite kit. FIG. 2B: In a similar setting, cells were collected and counted using a heamocytometer. Both experiments n=3, P>0.05

FIG. 5 is a series of images demonstrating the relationship and consistency between DKK2-null tumors, the hyperac-tivation of cytotoxic T cell (CTL) and the increase in apoptosis. Gut epithelial cells were stained by deoxynucle-otidyl transferase dUTP nick end labeling (TUNEL).

FIG. 8A: ELISA showing 5F8 and 1A10 recognizing rDKK2 (3 nM), but not rDKK1. FIG. 8B: Wnt inhibitory functions of DKK2 is reversed by 1A10 and 5F8 in a Wnt reporter assay on 293T-cells, 24 hrs.

FIG. 11 is a table listing the antigens used to immunize mice and their sequences. Two main antibodies were of particular interest (marked by a * or **): The antibody YAL008-1-5F8, against YAL008-1 antigen (SEQ ID NO 1), shows the highest affinity for the full-length DKK2 protein and was further characterized for neutralization activity. The antibody YAL008-5-1A10, against YAL008-5 antigen (SEQ ID NO 5) and the antibody YAL008-7-1A10, against YAL008-7 antigen (SEQ ID NO 7) recognizes the full-length DKK2 protein and has neutralization activity. The antibodies were generated from synthetic peptides by AbMax (AbMax Biotechnology Co., Ltd., China). While YAL008-5-1A10 and YAL008-7-1A10 were made from a sequence identical in both human and mouse DKK2, YAL008-1-5F8 is made from a human sequence, which has two residues different from the mouse one. YAL008-1-5F8 is still cross-reactive well to the mouse DKK2 protein. The affinities of both antibodies for the mouse DKK2 protein are at 0.1-1 nM range based on enzyme linked immunosorbant assay (ELISA). The sign "#" denotes the Cysteine residue added for conjugation. The amino acid sequences of the CDRs for YAL008-1-5F8, YAL008-5-1A10 and YAL008-7-1A10 (SEQ ID NOs: 8-13) are also listed below the table.

FIG. 20A demonstrates that in the Lewis lung carcinoma (LLC) allograft lung tumor model, YAL-008-1-5F8 had similar effect on tumor retardation as did PD-1 antibody; and the combination of YAL-008-1-5F8 and PD-1 antibody exhibited a higher suppression of tumor progression than with PD-1 antibody alone. FIG. 20B shows the comparative effect of YAL-008-1-5F8 on mouse survival when administered alone or in combination with other antibodies (Sigma IgG; PD-1 antibody) using the LLC allograft tumor model. FIG. 20C illustrates the comparative effect of YAL-008-1-5F8 on tumors formation when administered alone or in combination with other antibodies in the MC38 colon cancer model. In this MC38 model, PD-1 antibody has no significant effect on tumor formation.

DETAILED DESCRIPTION OF THE INVENTION

Figures 1A, 1B, 1C:
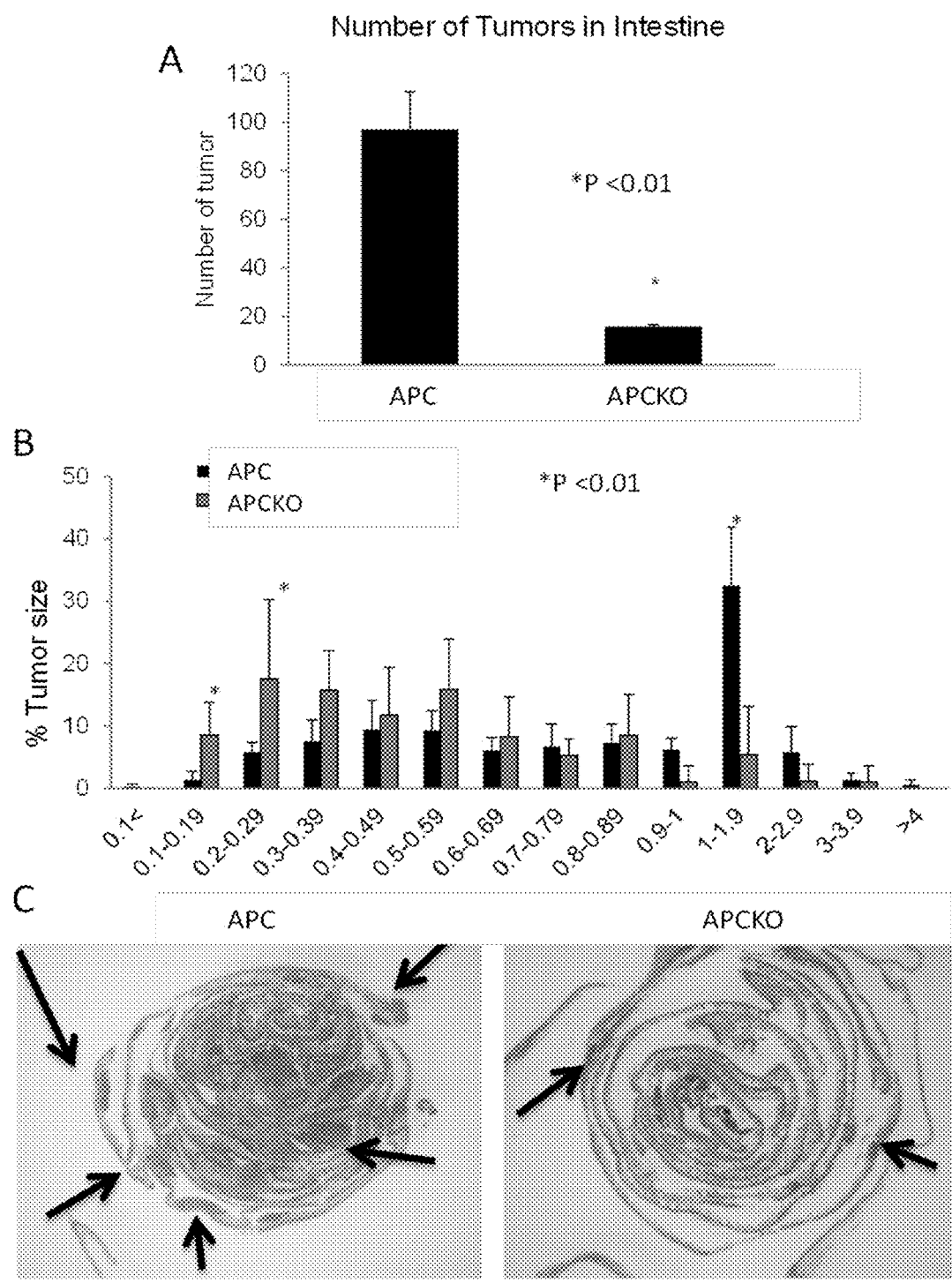
FIGS. 1A-1C are series of histograms and images illustrating the decreased tumor burden in APCKO (APC-minDKK2$^{-/-}$) mice. Littermate mice (male) were housed in SPF vivarium for 18 weeks on regular chow diet.

The present invention relates to the unexpected discovery that inhibition of Dickkopf2 (DKK2) results in suppression of tumors' formation accompanied by increased cytotoxic activity of immune effector cells including neutral killer (NK) cells and $CD8^+$ cytotoxic T lymphocytes (CTLs), and increased tumor cell apoptosis, and reduction in tumor angiogenesis. Thus, in various embodiments described herein, the methods of the invention relate to methods of treating cancer by administering to a patient an effective amount of DKK2 gene depleting agent, methods for providing anti-tumor immunity in a subject, methods of stimulating immune effector cell-mediated immune responses to a cell population or a tissue in a subject. Additionally, the current invention includes methods of diagnosing a cancer or a predisposition of developing a cancer and methods for determining the use of immunotherapy treatment for treating cancer. Furthermore, the invention encompasses a pharmaceutical composition for treating cancer as well as a kit for carrying out the aforementioned methods.

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, "10% greater" refers to expression levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween, than a control.

As used herein, the terms "control," or "reference" are used interchangeably, and refer to a value that is used as a standard of comparison (e.g., DKK2 level of expression in a healthy subject).

A "subject" or "patient," as used therein, may be a human or non-human mammal. Non-human mammals include, for example, livestock and pets, such as ovine, bovine, porcine, canine, feline and murine mammals. Preferably, the subject is human.

A "mutation" as used therein is a change in a DNA sequence resulting in an alteration from its natural state. The mutation can comprise deletion and/or insertion and/or duplication and/or substitution of at least one desoxyribonucleic acid base such as a purine (adenine and/or thymine) and/or a pyrimidine (guanine and/or cytosine) Mutations may or may not produce discernible changes in the observable characteristics (phenotype) of an organism (subject).

The term "immunogenicity" as used herein, is the ability of a particular substance, such as an antigen or epitope, to provoke an immune response in the body of a mammal. This immune response could be humoral and/or cell-mediated.

The term "activation", as used herein, refers to the state of a cell following sufficient cell surface moiety ligation to induce a noticeable biochemical or morphological change. Within the context of T cells, such activation refers to the state of a T cell that has been sufficiently stimulated to induce cellular proliferation. Activation of a T cell may also induce cytokine production and performance of regulatory or cytolytic effector functions. Within the context of other cells, this term infers either up or down regulation of a particular physico-chemical process The term "activated T cells" indicates T cells that are currently undergoing cell division, cytokine production, performance of regulatory or cytolytic effector functions, and/or has recently undergone the process of "activation."

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that may comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "RNA" as used herein is defined as ribonucleic acid.

The term the "immunotherapeutic agent" as used herein is meant to include any agent that modulates the patient's immune system. "immunotherapy" refers to the treatment that alters the patient's immune system.

The term "therapeutic" as used herein means a treatment and/or prophylaxis. A therapeutic effect is obtained by suppression, remission, or eradication of a disease state.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease. This includes prevention of cancer.

The term "biological sample" refers to a sample obtained from an organism or from components (e.g., cells) of an organism. The sample may be of any biological tissue or fluid. Frequently the sample will be a "clinical sample" which is a sample derived from a patient. Such samples include, but are not limited to, bone marrow, cardiac tissue, sputum, blood, lymphatic fluid, blood cells (e.g., white cells), tissue or fine needle biopsy samples, urine, peritoneal fluid, and pleural fluid, or cells therefrom. Biological samples may also include sections of tissues such as frozen sections taken for histological purposes.

"DKK protein" refers to a protein of the Dkk family of proteins that contains one or more cysteine-rich domains. The Dkk family of proteins includes Dkk1, Dkk2, Dkk3 and Dkk4, and any other protein sufficiently related to one or more of these proteins at the sequence level, structurally or functionally. This family of proteins is described, e.g., in Krupnik et al. (1999) Gene 238:301. Allelic variants and mutants of Dkk proteins such as those recited herein are also encompassed by this definition.

The term "equivalent," when used in reference to nucleotide sequences, is understood to refer to nucleotide sequences encoding functionally equivalent polypeptides. Equivalent nucleotide sequences will include sequences that differ by one or more nucleotide substitutions, additions- or deletions, such as allelic variants; and will, therefore, include sequences that differ from the nucleotide sequence of the nucleic acids described herein due to the degeneracy of the genetic code.

"Hybridization" refers to any process by which a strand of nucleic acid binds with a complementary strand through base pairing. Two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. Hybridization also includes the formation of duplexes which contain certain mismatches, provided that the two strands are still forming a double stranded helix. "Stringent hybridization conditions" refers to hybridization conditions resulting in essentially specific hybridization. The term "specific hybridization" of a probe to a target site of a template nucleic acid refers to hybridization of the probe predominantly to the target, such that the hybridization signal can be clearly interpreted. As further described herein, such conditions resulting in specific hybridization vary depending on the length of the region of homology, the GC content of the region, the melting temperature "Tm" of the hybrid. Hybridization conditions will thus vary in the salt content, acidity, and temperature of the hybridization solution and the washes.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. An "isolated cell" or "isolated population of cells" is a cell or population of cells that is not present in its natural environment.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

A "stem cell" refers to a cell that is capable of differentiating into a desired cell type. A stem cell includes embryonic stem (ES) cells; adult stem cells; and somatic stem cells, such as SP cells from uncommitted mesoderm. A "totipotent" stem cell is capable of differentiating into all tissue types, including cells of the meso-, endo-, and ectoderm. A "multipotent" or "pluripotent" stem cell is a cell which is capable of differentiating into at least two of several fates.

The term "variant," when used in the context of a polynucleotide sequence, may encompass a polynucleotide sequence related to that of a gene or the coding sequence thereof. This definition may also include, for example, "allelic," "splice," "species," or "polymorphic" variants. The polypeptides generally will have significant amino acid identity relative to each other. A polymorphic variant is a variation in the polynucleotide sequence of a particular gene between individuals of a given species. Polymorphic variants may encompass "single nucleotide polymorphisms" (SNPs) in which the polynucleotide sequence varies by one base. The presence of SNPs may be indicative of, for example, a certain population, a disease state, or a propensity for a disease state.

The term "Wnt antagonist" or "Wnt inhibitor" refers to a molecule or composition which downregulates (e.g., suppresses or inhibits) signal transduction via the Wnt pathway. Downregulation may occur directly, e.g., by inhibiting a bioactivity of a protein in a Wnt signaling pathway, or indirectly, e.g., by inhibiting downstream mediators of Wnt signaling (such as TCF3) or by decreasing stability of β-catenin, etc. Examples of Wnt antagonists include, but are not limited to, Dkk polypeptides (Glinka et al., Nature, 1998, 391: 357-62; Niehrs, Trends Genet, 1999, 15(8):314-9); crescent polypeptides (Marvin et al., Genes & Dev., 2001, 15: 316-327), cerberus polypeptides (U.S. Pat. No. 6,133,232), WISE/Sclerostin (Li et al., J Biol Chem, 2005. 280: 19883-7), axin polypeptides (Zeng et al., Cell, 1997, 90(1): 181-92; Itoh et al., Curr Biol, 1998, 8(10):591-4; Willert et al., Development, 1999, 126(18):4165-73), Frzb polypeptides (Cadigan et al., Cell, 1998, 93(5):767-77; U.S. Pat. Nos. 6,133,232; 6,485,972), glycogen synthase kinase (GSK) polypeptides (He et al., Nature, 1995) 374(6523): 617-22), T-cell factor (TCF) polypeptides (Molenaar et al., Cell, 1996, 86(3):391-9), dominant negative dishevelled polypeptides (Wallingford et al., Nature, 2000, 405(6782): 81-5), dominant negative N-cadherin polypeptides (U.S. Pat. No. 6,485,972), dominant negative β-catenin polypeptides (U.S. Pat. No. 6,485,972), dominant negatives of downstream transcription factors (e.g., TCF, etc.), dominant negatives of Wnt polypeptides, agents that disrupt LRP-frizzled-wnt complexes, and agents that sequester Wnts (e.g., crescent and antibodies to Wnts). Wnt antagonist polypeptides may be of mammalian origin, e.g., human, mouse, rat, canine, feline, bovine, or ovine, or non-mammalian origin, e.g., from Xenopus, zebrafish, Drosophila, chicken, or quail. Wnt antagonists also encompass fragments, homologs, derivatives, allelic variants, and peptidomimetics of various polypeptides, including, but not limited to, Dkk, crescent, cerberus, axin, Frzb, GSK, TCF, dominant negative dishevelled, dominant negative N-cadherin, and dominant negative β-catenin polypeptides. In other embodiments, Wnt antagonists also include antibodies (e.g., Wnt-specific antibodies), polynucleotides and small molecules.

The term "cancer" as used herein, includes any malignant tumor including, but not limited to, carcinoma, sarcoma. Cancer arises from the uncontrolled and/or abnormal division of cells that then invade and destroy the surrounding tissues. As used herein, "proliferating" and "proliferation" refer to cells undergoing mitosis. As used herein, "metastasis" refers to the distant spread of a malignant tumor from its sight of origin. Cancer cells may metastasize through the bloodstream, through the lymphatic system, across body cavities, or any combination thereof.

The term "carcinoma" refers to a malignant new growth made up of epithelial cells tending to infiltrate surrounding tissues, and to give rise to metastases.

The term "cancer vaccine" refers to a vaccine that stimulates the immune system to fight a cancer or to fight the agents that contribute to the development of a cancer. There are two broad types of cancer vaccines: Preventive cancer vaccines, which are intended to prevent cancer from developing in a healthy subject; and therapeutic cancer vaccines, which are intended to treat an existing cancer by strengthening the body's natural defenses against the cancer (Lollini et al., Nature Reviews Cancer, 2006; 6(3):204-216). As used herein the term "cancer vaccine" should be construed to include both preventive and therapeutic cancer vaccines.

The term "metastasis" refers to the spread of a cancer from one organ or part to another non-adjacent organ or part.

The term "angiogenesis" refers to the generation of new blood vessels, generally around or into a tissue or organ. Under normal physiological conditions, humans or animals undergo angiogenesis only in very specific restricted situations. For example, angiogenesis is normally observed in wound healing, fetal and embryonic development and formation of the corpus luteum, endometrium and placenta. Uncontrolled (persistent and/or unregulated) angiogenesis is related to various disease states, and occurs during tumor growth and metastasis.

The term "ameliorating" or "treating" means that the clinical signs and/or the symptoms associated with the cancer or melanoma are lessened as a result of the actions performed. The signs or symptoms to be monitored will be characteristic of a particular cancer or melanoma and will be well known to the skilled clinician, as will the methods for monitoring the signs and conditions. For example, the skilled clinician will know that the size or rate of growth of a tumor can monitored using a diagnostic imaging method typically used for the particular tumor (e.g., using ultrasound or magnetic resonance image (MRI) to monitor a tumor).

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

The term "antibody" or "Ab" as used herein, refers to a protein, or polypeptide sequence derived from an immunoglobulin molecule which specifically binds to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv) and humanized antibodies (Harlow et al., 1998, Using Antibodies: A Laboratory Manual, Cold Spring Harbor Laboratory Press, N.Y.; Harlow et al., 1989, Antibodies: A Laboratory Manual, Cold Spring Harbor, N.k.; Houston et al., 1988, Proc. Natl. Acad. Sci. USA 85:5879-5883; Bird et al., 1988, Science 242:423-426). An antibody may be derived from natural sources or from recombinant sources. Antibodies are typically tetramers of immunoglobulin molecules.

By the term "synthetic antibody" as used herein, is meant an antibody generated using recombinant DNA technology, such as, for example, an antibody expressed by a bacteriophage as described herein. The term should also be construed to mean an antibody generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either VL or VH), VHH domains, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

An "antibody heavy chain," as used herein, refers to the larger of the two types of polypeptide chains present in antibody molecules in their naturally occurring conformations, and which normally determines the class to which the antibody belongs.

An "antibody light chain," as used herein, refers to the smaller of the two types of polypeptide chains present in antibody molecules in their naturally occurring conformations. Kappa (κ) and lambda (λ) light chains refer to the two major antibody light chain isotypes.

By the term "recombinant antibody" as used herein, is meant an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

By the term "applicator," as the term is used herein, is meant any device including, but not limited to, a hypodermic syringe, a pipette, and the like, for administering the compounds and compositions of the invention.

As used herein, "aptamer" refers to a small molecule that can bind specifically to another molecule. Aptamers are typically either polynucleotide- or peptide-based molecules. A polynucleotide aptamer is a DNA or RNA molecule, usually comprising several strands of nucleic acids, that adopts highly specific three-dimensional conformation designed to have appropriate binding affinities and specificities towards specific target molecules, such as peptides, proteins, drugs, vitamins, among other organic and inorganic molecules. Such polynucleotide aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

The term "anti-tumor effect" as used herein, refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "xenograft" as used herein, refers to a graft of tissue taken from a donor of one species and grafted into a recipient of another species.

The term "allograft" as used herein, refers to a graft of tissue taken from a donor of one species and grafted into a recipient of the same species Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The immune system is balanced between activation and suppression. Evasion of immunosurvailence is one of the prerequisites for tumor formation. One of the ways for tumors to evade immunosurvailence is to produce elevated amount of immunosuppressive molecules. Increasing number of immunosuppressive molecules and mechanisms have been identified over the years. Neutralization of these immunosuppressive molecules has been shown to be efficacious in treating various malignancies.

The present invention relates to the discovery of a secreted tumor formation enhancer DKK2 that suppresses neutral killer (NK) cell and $CD8^+$ cytotoxic T lymphocyte (CTL) activity and stimulates tumor angiogenesis. DKK2 is a secreted protein, which can inhibit β-catenin-mediated Wnt signaling, alter non-β-catenin-mediated Wnt activity, and may also have Wnt-independent functions. It is also shown to have pro-angiogenic activity (Park et al., Angiogenesis, 2014. 17:221-34; Min et al., J Clin Invest, 2011. 121:1882-93). DKK2 is expressed in many tissues and is upregulated in human colorectal, gastric intestinal, liver, kidney, and pancreatic cancers. Experimental evidence described below indicates that DKK2 inhibitors and neutralizing antibodies are key immunomodulators and suppressors of tumor angiogenesis for treating cancers in which DKK2 is expressed. Thus DKK2 is a promising target for treating these cancers.

Methods of the Invention

The present invention is directed to a method of treating cancer in a subject in need thereof the method comprising administering to the subject an effective amount of a DKK2) gene depleting agent in a pharmaceutical acceptable carrier. By the term "DKK2 gene depleting agent" is meant any agent that inhibits or reduces expression of DKK2 or that inhibits or reduces DKK2 activity in a cell, tissue or bodily fluid.

Small Interfering RNA (siRNA)

In one embodiment, the depleting agent is a small interfering RNA (siRNA). siRNA is an RNA molecule comprising a set of nucleotides that is targeted to a gene or polynucleotide of interest. As used herein, the term "siRNA" encompasses all forms of siRNA including, but not limited to (i) a double stranded RNA polynucleotide, (ii) a single stranded polynucleotide, and (iii) a polynucleotide of either (i) or (ii) wherein such a polynucleotide, has one, two, three, four or more nucleotide alterations or substitutions therein. siRNAs and their use for inhibiting gene expression are well known in the art (Elbashir et al., Nature, 2001, 411 (6836): 494-988). In the present invention the siRNA is capable of interfering with the expression and/or the activity the gene of interest such as DKK2.

Ribozyme

In a further embodiment, the depleting agent is a ribozyme. Ribozymes and their use for inhibiting gene expression are also well known in the art (Cech et al., 1992, J. Biol. Chem. 267:17479-17482; Hampel et al, 1989, Biochemistry 28:4929-4933; Eckstein et al., International Publication No. WO 92/07065; Altaian et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific. There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules. Ribozymes useful for inhibiting the expression of a gene of interest (i.e. DKK2) may be designed by incorporating target sequences into the basic ribozyme structure which are complementary to the mRNA sequence of the desired gene. Ribozymes targeting the gene of interest may be synthesized using commercially available reagents (Applied Biosystems, Inc., Foster City, Calif.) or they may be genetically expressed from DNA encoding them.

Antisense Molecule

In another embodiment, the depleting agent is an antisense nucleic acid sequence. Antisense molecules and their use for inhibiting gene expression are well known in the art (Cohen, 1989, Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes. An antisense molecules may be provided to the cell via genetic expression using DNA encoding the antisense molecule as taught by Inoue, 1993, U.S. Pat. No. 5,190,931. Alternatively, antisense molecules may be made synthetically and then provided to the cell. Antisense oligomers of between about 10 to about 30, are preferred, since they are easily synthesized and introduced into a target cell. Synthetic antisense molecules contemplated by the invention include oligonucleotide derivatives known in the art which have improved biological activity compared to unmodified oligonucleotides (U.S. Pat. No. 5,023,243).

Small-Molecule Inhibitors

Figure 12:
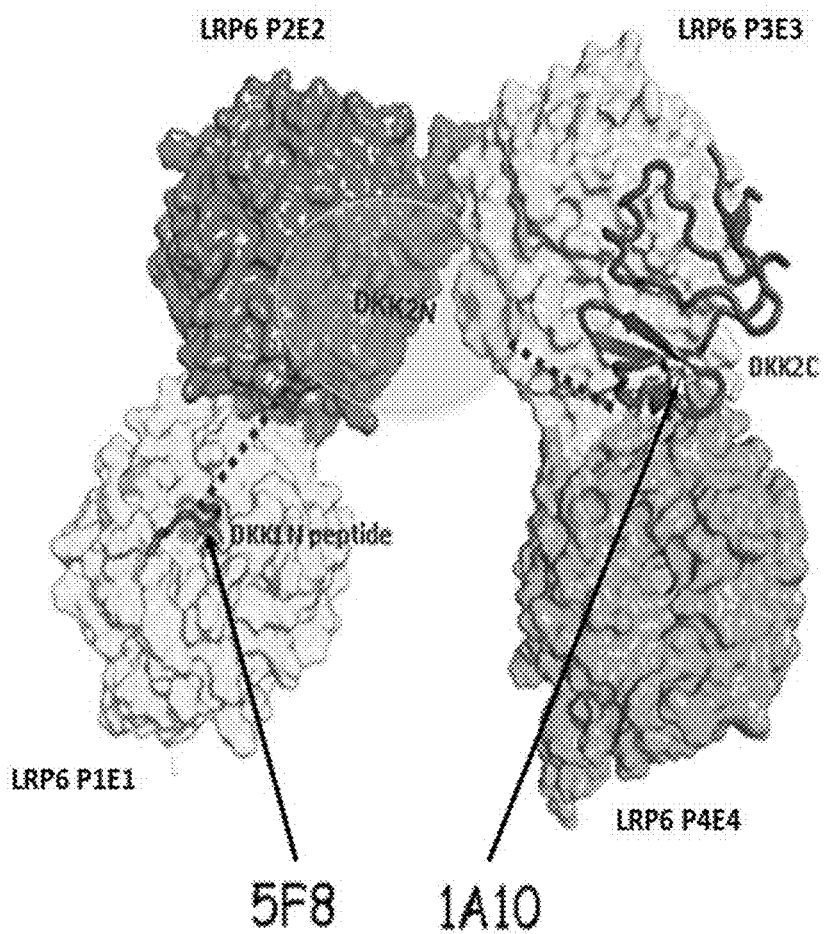
FIG. 12 is an image illustrating a proposed mechanism of DKK-LRP6 ectodomain interaction. All four beta-propellers of LRP6 ectodomain are shown in this representation. DKK (including N terminal peptide and DKK1C) are shown. The antigens for YAL008-1-5F8 (5F8) and YAL008-5-1A10 (1A10) Dkk2 neutralizing antibodies are denoted by the arrows.

It is well known in the art that some amino acid residues, located at the top cavity of the β-propeller structure of the third YWTD repeat domain of human LRP5, are important for DKK binding and DKK-mediated Wnt antagonism (Zhang et al., Mol Cell Biol. 2004; 24:4677-4684) (FIG. 12). In one embodiment of the present invention, a small molecule which can bind to this cavity and disrupt the interaction between DKK and LRP5/6, acts as a DKK2 inhibiting agent. In a specific embodiment, the DKK2 inhibiting agent is any small-molecule analogous to any amino acid residue of LRP5 known in the art to be involved in DKK binding. Non limiting examples of those residues are Glu721, Trp863, Tyr719, Arg764, Asp887, Phe888, Gly781, Trp780, and Met890 (Zhang et al., Mol Cell Biol. 2004; 24:4677-4684). In a further embodiment, the small-molecule acting as DKK2 inhibitor is a gallocyanine compound (e.g. IIC8 and IIIC3) (Li et al., Proc Natl Acad Sci USA, 2012. 109: 11402-7).

Antibodies

The invention contemplates using a composition comprising an anti-DKK2 antibody. In one embodiment, the antibody comprises an antibody selected from a polyclonal antibody, a monoclonal antibody, a humanized antibody, a synthetic antibody, a heavy chain antibody, a human antibody, and a biologically active fragment of an antibody and any combination thereof. In a specific embodiment, the synthetic antibody is produced by AbMax Biotechnology Co. Ltd. (China) such as the antibody YAL008-1-5F8 (with an antigen peptide sequence being 5'-KLNSIKSSLG-GETPG-3', SEQ ID NO 1, located at the N-terminus of DKK2), located at the N-terminus of DKK2), the antibody YAL008-5-1A10 (with an antigen peptide sequence being 5'-CKVWKDATYSSKAR-3', SEQ ID NO 5, located at the second Cys-rich domain of DKK2), and the antibody YAL008-7-1A10 (with an antigen peptide sequence being 5'-CARHFWTKIC-3', SEQ ID NO 7, located at the second Cys-rich domain of DKK2) (FIGS. 11 and 12). In a further embodiment, a cysteine ("C") is added on the 3' end of the antigen peptide for conjugation.

Methods of producing antibodies are known in the art. Exemplary techniques for the production of the antibodies used in accordance with the present invention are herein described. It will be appreciated by one skilled in the art that an antibody comprises any immunoglobulin molecule, whether derived from natural sources or from recombinant sources, which is able to specifically bind to an epitope present on a target molecule. In one embodiment, the target molecule comprises When the antibody to the target molecule used in the compositions and methods of the invention is a polyclonal antibody (IgG), the antibody is generated by inoculating a suitable animal with a peptide comprising full length target protein, or a fragment thereof, an upstream regulator, or fragments thereof. These polypeptides, or fragments thereof, may be obtained by any methods known in the art, including chemical synthesis and biological synthesis.

Antibodies produced in the inoculated animal that specifically bind to the target molecule, or fragments thereof, are then isolated from fluid obtained from the animal. Antibodies may be generated in this manner in several non-human mammals such as, but not limited to goat, sheep, horse, camel, rabbit, and donkey. Methods for generating polyclonal antibodies are well known in the art and are described, for example in Harlow et al., 1998, In: Antibodies, A Laboratory Manual, Cold Spring Harbor, N.Y.

Monoclonal antibodies directed against a full length target molecule, or fragments thereof, may be prepared using any well-known monoclonal antibody preparation procedures, such as those described, for example, in Harlow et al. (1998, In: Antibodies, A Laboratory Manual, Cold Spring Harbor, N.Y.) and in Tuszynski et al. (1988, Blood, 72:109-115). Human monoclonal antibodies may be prepared by the method described in U.S. Patent Publication No. 2003/0224490. Monoclonal antibodies directed against an antigen are generated from mice immunized with the antigen using standard procedures as referenced herein. Nucleic acid encoding the monoclonal antibody obtained using the procedures described herein may be cloned and sequenced using technology which is available in the art, and is described, for example, in Wright et al., 1992, Critical Rev. Immunol. 12(3,4):125-168, and the references cited therein.

When the antibody used in the methods of the invention is a biologically active antibody fragment or a synthetic antibody corresponding to antibody to a full length target molecule, or fragments thereof, the antibody is prepared as follows: a nucleic acid encoding the desired antibody or fragment thereof is cloned into a suitable vector. The vector is transfected into cells suitable for the generation of large quantities of the antibody or fragment thereof. DNA encoding the desired antibody is then expressed in the cell thereby producing the antibody. The nucleic acid encoding the desired peptide may be cloned and sequenced using technology available in the art, and described, for example, in Wright et al., 1992, Critical Rev. in Immunol. 12(3,4): 125-168 and the references cited therein. Alternatively, quantities of the desired antibody or fragment thereof may also be synthesized using chemical synthesis technology. If the amino acid sequence of the antibody is known, the desired antibody can be chemically synthesized using methods known in the art.

The present invention also may include the use of humanized antibodies specifically reactive with an epitope present on a target molecule. These antibodies are capable of binding to the target molecule. The humanized antibodies useful in the invention have a human framework and have one or more complementarity determining regions (CDRs) from an antibody, typically a mouse antibody, specifically reactive with a targeted cell surface molecule. The amino acid sequences of the CDRs sequences for YAL008-1-5F8, YAL008-5 1A10 and YAL008-7-1A10 are listed in FIG. 11.

When the antibody used in the invention is humanized, the antibody can be generated as described in Queen et al. (U.S. Pat. No. 6,180,370), Wright et al., 1992, Critical Rev. Immunol. 12(3,4):125-168, and in the references cited therein, or in Gu et al., 1997, Thrombosis & Hematocyst 77(4):755-759, or using other methods of generating a humanized antibody known in the art. The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to humanized immunoglobulin coding sequences, including naturally-associated or heterologous promoter regions. The expression control sequences can be eukaryotic promoter systems in vectors capable of transforming or transfecting eukaryotic host cells, or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, 1979, which is incorporated herein by reference).

DNA sequences of human antibodies and particularly the complementarity determining regions (CDRs) can be isolated in accordance with procedures well known in the art. Preferably, the human CDRs DNA sequences are isolated from immortalized B-cells as described in International Patent Application Publication No. WO 1987/02671. CDRs useful in producing the antibodies of the present invention may be similarly derived from DNA encoding monoclonal antibodies capable of binding to the target molecule. Such humanized antibodies may be generated using well-known methods in any convenient mammalian source capable of producing antibodies, including, but not limited to, mice, rats, camels, llamas, rabbits, or other vertebrates. Suitable cells for constant region and framework DNA sequences and host cells in which the antibodies are expressed and secreted, can be obtained from a number of sources, such as the American Type Culture Collection, Manassas, Va.

Another method of generating specific antibodies, or antibody fragments, reactive against a DKK2 involves the screening of expression libraries encoding immunoglobulin genes, or portions thereof, expressed in bacteria with a DKK2 protein or peptide. For example, complete Fab fragments, VH regions and Fv regions can be expressed in bacteria using phage expression libraries. See for example, Ward et al., Nature, 1989, 341:544-546; Huse et al., Science, 1989, 246:1275-1281; and McCafferty et al., Nature, 1990, 348: 552-554. Screening such libraries with, for example, a DKK2 peptide, can identify immunoglobulin fragments reactive with DKK2. Alternatively, the SCID-hu mouse (available from Genpharm) can be used to produce antibodies or fragments thereof.

In a further embodiment, antibodies or antibody fragments can be isolated from antibody phage libraries generated using the techniques described in McCafferty et al., Nature, 1990, 348:552-554. Clackson et al., Nature, 1991, 352:624-628 and Marks et al., J Mol Biol, 1991, 222:581-597 describe the isolation of murine and human antibodies, respectively, using phage libraries. Subsequent publications describe the production of high affinity (nM range) human antibodies by chain shuffling (Marks et al., BioTechnology, 1992, 10: 779-783), as well as combinatorial infection and in vivo recombination as a strategy for constructing very large phage libraries (Waterhouse et al., Nuc. Acids. Res., 1993, 21: 2265-2266). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 1984, 81: 6851), or by covalently joining to the immunoglobulin coding sequence all or part of the coding sequence for a non-immunoglobulin polypeptide. Typically, such non-immunoglobulin polypeptides are substituted for the constant domains of an antibody, or they are substituted for the variable domains of one antigen combining site of an antibody to create a chimeric bivalent antibody having one antigen-combining site with specificity for a first antigen and another antigen-combining site with specificity for a different antigen.

Various techniques have been developed for the production of functional antibody fragments. The antibody fragment may include a variable region or antigen-binding region of the antibody. Traditionally, these fragments were derived via proteolytic digestion of intact antibodies (see, e.g., Morimoto et al., Journal of Biochemical and Biophysical Methods, 1992, 24: 107-117 and Brennan et al., Science, 1985, 229: 81). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F (ab') 2 fragments (Carter et al., Bio/Technology, 1992, 10: 163-167). According to another approach, F (ab') 2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody", e.g., as described in U.S. Pat. No. 5,641,870 for example. Such linear antibody fragments may be monospecific or bispecific.

Antibody mimics or "non-antibody binding protein" use non-immunoglobulin protein scaffolds, including adnectins, avimers, single chain polypeptide binding molecules, and antibody-like binding peptidomimetics by using non-immunoglobulin protein scaffolds as alternative protein frameworks for the variable regions of antibodies (U.S. Pat. Nos. 5,260,203; 5,770,380; 6,818,418 and 7,115,396). Other compounds have been developed that target and bind to targets in a manner similar to antibodies. Certain of these "antibody mimics" use non-immunoglobulin protein scaffolds as alternative protein frameworks for the variable regions of antibodies. A methodology for reducing antibodies into smaller peptidomimetics, termed "antibody like binding peptidomimetics" (ABiP) can be used, a methodology for reducing antibodies into smaller peptidomimetics, can also be useful as an alternative to antibodies (Murali et al. Cell Mol Biol., 2003, 49(2):209-216).

Fusion proteins that are single-chain polypeptides including multiple domains termed "avimers" were developed from human extracellular receptor domains by in vitro exon shuffling and phage display and are a class of binding proteins somewhat similar to antibodies in their affinities and specificities for various target molecules (Silverman et al. Nat Biotechnol, 2005, 23: 1556-1561). The resulting multidomain proteins can include multiple independent binding domains that can exhibit improved affinity (in some cases sub-nanomolar) and specificity compared with single-epitope binding proteins. Additional details concerning methods of construction and use of avimers are disclosed, for example, in US Pat. App. Pub. Nos. 20040175756, 20050048512, 20050053973, 20050089932 and 20050221384.

In addition to non-immunoglobulin protein frameworks, antibody properties have also been mimicked in compounds including, but not limited to, RNA molecules and unnatural oligomers (e.g., protease inhibitors, benzodiazepines, purine derivatives and beta-turn mimics) all of which are suitable for use with the present invention. These are aimed to circumvent the limitations of developing antibodies in animals by developing wholly in vitro techniques for designing antibodies of tailored specificity.

As known in the art, aptamers are macromolecules composed of nucleic acid that bind tightly to a specific molecular target. Tuerk and Gold (Science, 1990, 249:505-510) discloses SELEX (Systematic Evolution of Ligands by Exponential Enrichment) method for selection of aptamers. In the SELEX method, a large library of nucleic acid molecules (e.g., 1015 different molecules) is produced and/or screened with the target molecule. Isolated aptamers can then be further refined to eliminate any nucleotides that do not contribute to target binding and/or aptamer structure (i.e., aptamers truncated to their core binding domain). See, e.g., Jayasena, 1999, Clin. Chem. 45:1628-1650 for review of aptamer technology.

The term "neutralizing" in reference to an anti-DKK2 antibody of the invention or the phrase "antibody that neutralizes DKK2 activity" is intended to refer to an antibody whose binding to or contact with DKK2 results in inhibition of a cell proliferative activity, metastasis of cancer, invasion of cancer cells or migration of cancer cells, inhibition of Wnt signaling, angiogenesis, establishment of tumor-formation promoting microenvironment induced by DKK2. Because the DKK2 is secreted to extracellular and functions as an essential factor of proliferation, migration, invasion and metastasis of cancer cells, some anti-DKK2 antibodies may neutralize these activity. The neutralizing antibody in this invention is especially useful in therapeutic applications: to prevent or treat intractable diseases cancers, and cancer metastasis. The neutralizing antibody in this invention can be administered to a patient, or contacted with a cell for inhibiting metastasis of a cancer characterized by the over-expression of DKK2.

The antibody of the present invention can be assessed for immunospecific binding by any method known in the art. The immunoassays that can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g, Current Protocols in Molecular Biology, (Ausubel et al., eds.), Greene Publishing Associates and Wiley-Interscience, New York, 2002).

Combination Therapies

The compounds identified in the methods described herein may also be useful in the methods of the invention when combined with at least one additional compound useful for treating cancer. The additional compound may comprise a compound identified herein or a compound, e.g., a commercially available compounds, known to treat, prevent, or reduce the symptoms of cancer and/or metastasis.

In one aspect, the present invention contemplates that the agents useful within the invention may be used in combination with a therapeutic agent such as an anti-tumor agent, including but not limited to a chemotherapeutic agent, immunotherapeutic agent, an anti-cell proliferation agent or any combination thereof. For example, any conventional chemotherapeutic agents of the following non-limiting exemplary classes are included in the invention: alkylating agents; nitrosoureas; antimetabolites; antitumor antibiotics; plant alkyloids; taxanes; hormonal agents; and miscellaneous agents.

Alkylating agents are so named because of their ability to add alkyl groups to many electronegative groups under conditions present in cells, thereby interfering with DNA replication to prevent cancer cells from reproducing. Most alkylating agents are cell cycle non-specific. In specific aspects, they stop tumor growth by cross-linking guanine bases in DNA double-helix strands. Non-limiting examples include busulfan, carboplatin, chlorambucil, cisplatin, cyclophosphamide, dacarbazine, ifosfamide, mechlorethamine hydrochloride, melphalan, procarbazine, thiotepa, and uracil mustard.

Anti-metabolites prevent incorporation of bases into DNA during the synthesis (S) phase of the cell cycle, prohibiting normal development and division. Non-limiting examples of antimetabolites include drugs such as 5-fluorouracil, 6-mercaptopurine, capecitabine, cytosine arabinoside, floxuridine, fludarabine, gemcitabine, methotrexate, and thioguanine.

Antitumor antibiotics generally prevent cell division by interfering with enzymes needed for cell division or by altering the membranes that surround cells. Included in this class are the anthracyclines, such as doxorubicin, which act to prevent cell division by disrupting the structure of the DNA and terminate its function. These agents are cell cycle non-specific. Non-limiting examples of antitumor antibiotics include aclacinomycin, actinomycin, anthramycin, azaserine, bleomycins, cactinomycin, calicheamicin, carubicin, caminomycin, carzinophilin, chromomycin, dactinomycin, daunorubicin, detorubicin, 6-diazo-5-oxo-L-norleucine, doxorubicin, epirubicin, esorubicin, idarubicin, marcellomycin, mitomycins, mitoxantrone, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin.

Plant alkaloids inhibit or stop mitosis or inhibit enzymes that prevent cells from making proteins needed for cell growth. Frequently used plant alkaloids include vinblastine, vincristine, vindesine, and vinorelbine. However, the invention should not be construed as being limited solely to these plant alkaloids.

The taxanes affect cell structures called microtubules that are important in cellular functions. In normal cell growth, microtubules are formed when a cell starts dividing, but once the cell stops dividing, the microtubules are disassembled or destroyed. Taxanes prohibit the microtubules from breaking down such that the cancer cells become so clogged with microtubules that they cannot grow and divide. Non-limiting exemplary taxanes include paclitaxel and docetaxel.

Hormonal agents and hormone-like drugs are utilized for certain types of cancer, including, for example, leukemia, lymphoma, and multiple myeloma. They are often employed with other types of chemotherapy drugs to enhance their effectiveness. Sex hormones are used to alter the action or production of female or male hormones and are used to slow the growth of breast, prostate, and endometrial cancers. Inhibiting the production (aromatase inhibitors) or action (tamoxifen) of these hormones can often be used as an adjunct to therapy. Some other tumors are also hormone dependent. Tamoxifen is a non-limiting example of a hormonal agent that interferes with the activity of estrogen, which promotes the growth of breast cancer cells.

Miscellaneous agents include chemotherapeutics such as bleomycin, hydroxyurea, L-asparaginase, and procarbazine.

Other examples of chemotherapeutic agents include, but are not limited to, the following and their pharmaceutically acceptable salts, acids and derivatives: nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, ranimustine; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatrexate; defofamine; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK@ razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOLO, Bristol-Myers Squibb Oncology, Princeton, N.J.) and docetaxel (TAXOTERE, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; and capecitabine.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof.

In additional aspects, the caspase is caspase-1, caspase-2, caspase-3, caspase-4, caspase-5, caspase-6, caspase-7, caspase-8, caspase-9, caspase-10, caspase-11, caspase-12, caspase-13, caspase-14, or a combination thereof. In specific aspects, the cytotoxic agent is TNF-α, gelonin, Prodigiosin, a ribosome-inhibiting protein (RIP), *Pseudomonas* exotoxin, *Clostridium difficile* Toxin B, *Helicobacter pylori* VacA, *Yersinia enterocolitica* YopT, Violacein, diethylenetriaminepentaacetic acid, irofulven, Diptheria Toxin, mitogillin, ricin, botulinum toxin, cholera toxin, saporin 6, or a combination thereof.

An immunotherapeutic agent may be, but is not limited to, an interleukin-2 or other cytokine, an inhibitor of programmed cell death protein 1 (PD-1) signaling such as a monoclonal antibody that binds to PD-1, Ipilimumab. The immunotherapeutic agent can also block cytotoxic T lymphocytes associated antigen A-4 (CTLA-4) signaling and it can also relate to cancer vaccines and dendritic cell-based therapies.

The immunotherapeutic agent can further be NK cells that are activated and expanded by means of cytokine treatment or by transferring exogenous cells by adoptive cell therapy and/or by hematopoietic stem cell transplantation. NK cells suitable for adoptive cell therapy can be derived from different sources, including ex vivo expansion of autologous NK cells, unstimulated or expanded allogeneic NK cells from peripheral blood, derived from CD34+ hematopoietic progenitors from peripheral blood and umbilical cord blood, and NK-cell lines. Genetically modified NK cells expressing chimeric antigen receptors or cytokines are also contemplated in this invention. Another immunotherapeutic agent useful for this invention is an agent based on adoptive T cell therapy (ACT) wherein tumor-infiltrating lymphocytes (TILs) are administered to patients. The administered T cells can be genetically engineered to express tumor-specific antigen receptors such as chimeric antigen receptors (CARs), which recognize cell-surface antigens in a non-major histocompatibility (MHC)-restricted manner; or they can be traditional αβ TCRs, which recognize epitopes of intracellular antigens presented by MHC molecules.

Pharmaceutical Compositions and Formulations

The invention envisions the use of a pharmaceutical composition comprising a DKK2 depleting agent for use in the methods of the invention.

Such a pharmaceutical composition is in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions are formulated using one or more pharmaceutically acceptable excipients or carriers. In one embodiment, the pharmaceutical compositions comprise a therapeutically effective amount of DKK2 depleting agent and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences, 1991, Mack Publication Co., New Jersey.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Administration/Dosing

The regimen of administration may affect what constitutes an effective amount. For example, the therapeutic formulations may be administered to the patient either prior to or after a surgical intervention related to cancer, or shortly after the patient was diagnosed with cancer. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat cancer in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the animal. Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient. A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of cancer in a patient.

Routes of Administration

One skilled in the art will recognize that although more than one route can be used for administration, a particular route can provide a more immediate and more effective reaction than another route.

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration. Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, which are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Immune Response Stimulation

In one embodiment, the invention comprises methods for providing anti-tumor immunity and for stimulating T-cell mediated immune response by administering the to the subject an effective amount of a DKK2 antibody or fragment thereof with a pharmaceutical acceptable carrier.

The activation T lymphocytes (T cells) and its use within immunotherapy for the treatment of cancer and infectious diseases, is well known in the art (Melief et al., Immunol. Rev., 1995, 145:167-177; Riddell et al., Annu. Rev. Immunol., 1995, 13:545-586). As disclosed in the current invention, elimination of DKK2 leads to an activation of CD8+ cytotoxic T lymphocytes (CTL) and suppression of tumors.

Markers for CTL activation could be, but are not limited to, cytotoxins such as perforin, granzymes, and granulysin, cytokines, IL-2, IL-4, CD25, CD54, CD69, CD38, CD45RO, CD49d, CD40L, CD137, CD134. The measurement in a sample of level of at least one of these markers can be used to assess CTL activation as presented herein the Examples section. Sorting of T cells, or generally any cells of the present invention, can be carried out using any of a variety of commercially available cell sorters, including, but not limited to, MoFlo sorter (DakoCytomation, Fort Collins, Colo.), FACSAria™, FACSArray™ FACSVantage™, BD™ LSR II, and FACSCalibur™ (BD Biosciences, San Jose, Calif.).

Angiogenesis

Angiogenesis is a normal and vital process in growth and development, as well as in wound healing and in the formation of granulation tissue. The normal regulation of angiogenesis is governed by a fine balance between factors that induce the formation of blood vessels and those that halt or inhibit the process. When this balance is destroyed, it usually results in pathological angiogenesis which causes increased blood-vessel formation. Pathological angiogenesis is a hallmark of cancer and various ischaemic and inflammatory diseases (e.g. cardiovascular diseases). As tumors cannot grow beyond a certain size or spread without a blood supply, blocking tumor angiogenesis is an effective approach in anticancer therapy. Also the use of angiogenesis inhibitors, also referred to as anti-angiogenic agents, in known in the art as relevant for treating ischaemic and inflammatory diseases. In one embodiment of the present invention, the DKK2 depleting agent is an angiogenesis inhibitor that prevents or slows the growth of cancer. In another embodiment, the DKK2 depleting agent is an anti-angiogenic agent, that prevents or treat ischaemic and inflammatory diseases. Non limiting examples of inflammatory diseases are cardiovascular diseases, atherosclerosis and rheumatoid arthritis.

Diagnosis and Treatment

In one embodiment, the invention relates to a method of diagnosing a cancer or a predisposition for developing a cancer or a metastasis in a subject. The method comprises determining the expression level of DKK2 gene in a biological sample from the subject, wherein an increase in the expression level of DKK2 as compared with a normal control level of DKK2 expression is an indication that the subject has cancer or has a predisposition for developing a cancer or metastasis.

In another embodiment, the invention relates to a method for determining the efficacy of immunotherapy treatment for treating cancer in a subject in need thereof. The method comprises determining the expression level of DKK2 gene in a biological sample from the subject, wherein an increase in the expression level of DKK2 as compared with the expression level of DKK2 in a normal control is an indication that immunotherapy treatment will effective. In some aspects of the invention, treatment of cancer may include the treatment of solid tumors or the treatment of metastasis. Metastasis is a form of cancer wherein the transformed or malignant cells are traveling and spreading the cancer from one site to another. Such cancers include cancers of the skin, breast, brain, cervix, testes, etc. More particularly, cancers may include, but are not limited to the following organs or systems: cardiac, lung, gastrointestinal, genitourinary tract, liver, bone, nervous system, gynecological, hematologic, skin, and adrenal glands. More particularly, the methods herein can be used for treating gliomas (Schwannoma, glioblastoma, astrocytoma), neuroblastoma, pheochromocytoma, paraganlioma, meningioma, adrenalcortical carcinoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia. Skin cancer includes malignant melanoma, basal cell carcinoma, squamous cell carcinoma, Karposi's sarcoma, moles dysplastic nevi, lipoma, angioma, dermatofibroma, keloids, and psoriasis.

Control Standard Amount of Expression of the Gene of Interest (DKK2)

The method of the invention includes comparing a measured amount of expression of DKK2 in a biological sample from a subject to a control amount (i.e. the reference) of expression of DKK2.

In one embodiment, the standard control level of expression of DKK2 may be obtained by measuring the expression level of DKK2 in a healthy subject. Preferably, the healthy subject is a subject of similar age, gender and race and has never been diagnosed with any type of sever disease particularly any type of cancer.

In another embodiment, the control amount of expression of DKK2 is a value for expression of DKK2 that is accepted in the art. This reference value can be baseline value calculated for a group of subjects based on the average or mean values of DKK2 expression by applying standard statistically methods.

In one embodiment, the expression level is determined by a method selected from the group consisting of detecting mRNA of the gene, detecting a protein encoded by the gene, and detecting a biological activity of the protein encoded by the gene.

In certain aspects of the present invention, the expression level of DKK2 is determined in a sample from a subject. The sample preferably includes tumor cells, any fluid from the surrounding of tumor cells (i.e., leukemic blood, tumor tissue, etc . . . ) or any fluid that is in physiological contact or proximity with the tumor, or any other body fluid in addition to those recited herein should also be considered to be included in the invention.

Methods of Measurement

Any method known to those in the art can be employed for determining the level of DKK2 expression. For example, a microarray can be used. Microarrays are known in the art and consist of a surface to which probes that correspond in sequence to gene products (e.g. mRNAs, polypeptides, fragments thereof etc.) can be specifically hybridized or bound to a known position. To detect at least one gene of interest, a hybridization sample is formed by contacting the test sample with at least one nucleic acid probe. A preferred probe for detecting DKK2 is a labeled nucleic acid probe capable of hybridizing to DKK2 mRNA. The nucleic acid probe can be, for example, a full-length nucleic acid molecule, or a portion thereof, such as an oligonucleotide of at least 10, 15, or 20 nucleotides in length and sufficient to specifically hybridize under stringent conditions to the appropriate target. The hybridization sample is maintained under conditions which are sufficient to allow specific hybridization of the nucleic acid probe to a target of interest. Specific hybridization can be performed under high stringency conditions or moderate stringency conditions, as appropriate. In a preferred embodiment, the hybridization conditions for specific hybridization are high stringency. Specific hybridization, if present, is then detected using standard methods. If specific hybridization occurs between the nucleic acid probe and a gene in the test sample, the sequence that is present in the nucleic acid probe is also present in the mRNA of the subject. More than one nucleic acid probe can also be used. Hybridization intensity data detected by the scanner are automatically acquired and processed by the Affymetrix Microarray Suite (MASS) software. Raw data is normalized to expression levels using a target intensity of 150. An alternate method to measure mRNA expression profiles of a small number of different genes is by e.g. either classical TaqMan® Gene Expression Assays or TaqMan® Low Density Array—micro fluidic cards (Applied Biosystems). Particularly, this invention preferably utilizes a qPCR system. Non-limiting examples include commercial kits such as the PrimePCRPathways® commercially available from Bio-rad (Berkley, Calif.).

The transcriptional state of a sample, particularly mRNAs, may also be measured by other nucleic acid expression technologies known in the art. mRNA can be isolated from the sample using any method known to those in the art. Non-limiting examples include commercial kits, such as the RNeasy® commercially available from Qiagen (Netherlands) or the Mini Kit the TRI Reagent® commercially available from Molecular Research Center, Inc. (Cincinnati, Ohio), can be used to isolate RNA. Generally, the isolated mRNA may be amplified using methods known in the art. Amplification systems utilizing, for example, PCR or RT-PCR methodologies are known to those skilled in the art. For a general overview of amplification technology, see, for example, Dieffenbach et al., PCR Primer: A Laboratory Manual, Cold Spring Harbor Laboratory Press, N.Y. (1995).

Another accurate method for profiling mRNA expression can the use of Next Generation Sequencing (NGS) including first, second, third as well as subsequent Next Generations Sequencing technologies.

In other aspects of the present invention, determining the amount or detecting the biological activity of a peptide, polypeptide can be achieved by all known means in the art for determining the amount of a peptide or polypeptide in a sample. These means comprise immunoassay devices and methods which may utilize labeled molecules in various sandwich, competition, or other assay formats. Such assays will develop a signal which is indicative for the presence or absence of the peptide or polypeptide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Kit

The invention includes a set of preferred antibodies, either labeled (e.g., fluorescer, quencher, etc.) or unlabeled, that are useful for the detection of at least DKK2.

In certain embodiments, a kit is provided. Commercially available kits for use in these methods are, in view of this specification, known to those of skill in the art. In general, kits will comprise a detection reagent that is suitable for detecting the presence of a polypeptide or nucleic acid, or mRNA of interest.

In another embodiment, there is a panel of probe sets or antibodies. In some embodiments, the panel of antibodies comprises a neutralizing DKK2 antibody targeting a DKK2 epitope comprising at least one of the amino acid sequences selected from the group consisting of KLNSIKSSLG-GETPG (SEQ ID NO 1), CKVWKDATYSSKAR (SEQ ID NO 5) and CARHFWTKIC (SEQ ID NO 7). In some embodiments, the panel of probe sets is designed to detect the level of DKK2 and provide information about cancer diagnosis or the predisposition of developing a cancer or a metastasis. Probe sets are particularly useful because they are smaller and cheaper than probe sets that are intended to detect as many peptides as possible in a particular genome. In the present invention, the probe sets are targeted at the detection of polypeptides that are informative about cancer genes. Probe sets may also comprise a large or small number of probes that detect peptides that are not informative about cancer. Such probes are useful as controls and for normalization (e.g., spiked-in markers). Probe sets may be a dry mixture or a mixture in solution. In some embodiments, probe sets can be affixed to a solid substrate to form an array of probes. The probes may be antibodies, or nucleic acids (e.g., DNA, RNA, chemically modified forms of DNA and RNA), LNAs (Locked nucleic acids), or PNAs (Peptide nucleic acids), or any other polymeric compound capable of specifically interacting with the peptides or nucleic acid sequences of interest.

It is contemplated that kits may be designed for isolating and/or detecting peptides (e.g. DKK2, know cancer markers, immune activators or apoptotic proteins) or nucleic acid sequences in essentially any sample (e.g., leukemic blood, tumor cells, tumor tissue, etc.), and a wide variety of reagents and methods are, in view of this specification, known in the art.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Figures 2A, 2B:
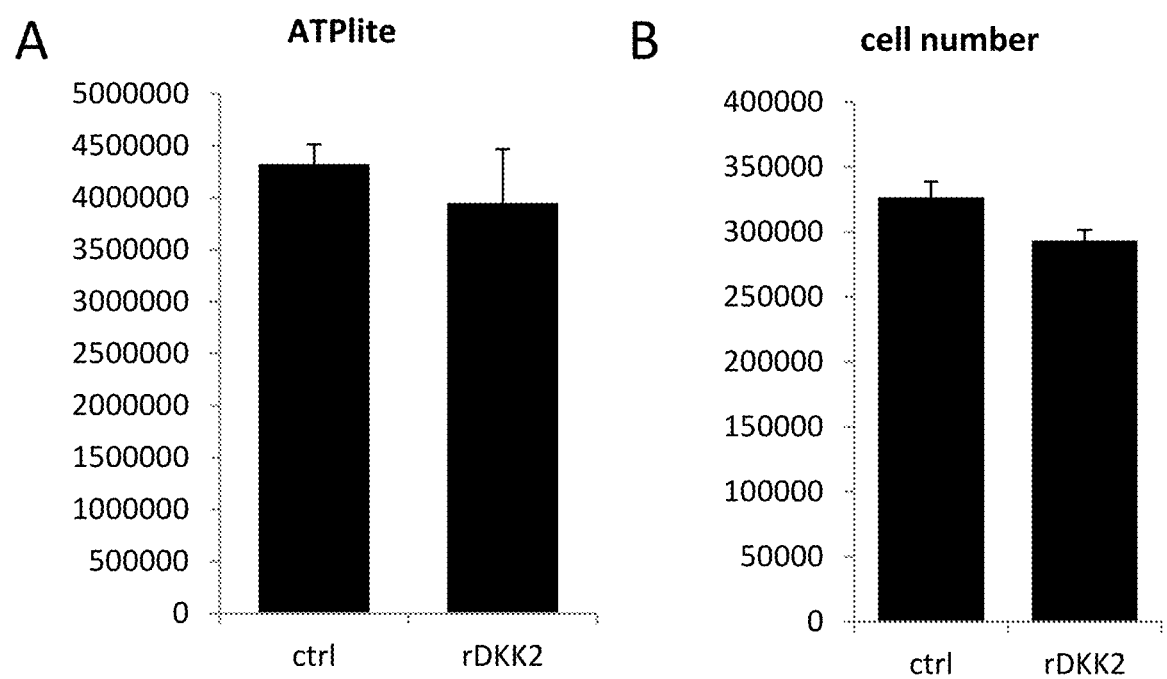
FIGS. 2A-2B are histograms demonstrating that DKK2 does not regulate proliferation in MC38 cells.

Example 1: Genetic DKK2 Deletion Leads to Reduced Tumor Burden in APC$^{Min/+}$ Mice APC$^{Min/+}$ mice (designated APC) and APC$^{Min/+}$ DKK2$^{-/-}$ (APCKO) mice were housed in a specific pathogen free vivarium. In the absence of DKK2, tumor progression was significantly reduced as indicated by lower tumor number and size (FIGS. 1A and 1B). In accordance, tumor induced abnormalities such as splenomegaly, thymic atrophy and lymphopenia (You, S., et al., Int J Exp Pathol, 2006. 87(3): p. 227-36) were significantly lower in APCKO mice. This phenomenon was seen in groups of male and female mice on both high and low fat diets with consistent results. Together, these data strongly suggests that in the absence of DKK2, colon cancer progression is significantly lower. Since some studies have linked DKK2 to increased or decreased proliferation of tumor cells (Hirata, H., et al., Clin Cancer Res, 2009. 15(18): p. 5678-87; Hauer, K., et al., Cancer Res, 2013. 73(2): p. 967-77), DKK2 was tested for its potential involvement promoting proliferation. In this investigation, Mouse colon carcinoma MC38 cells (Mayo Clinic) were treated with recombinant DKK2 (rDKK2) 24 hours later, then the effect on cell proliferation was measured using both an ATPlite kit (PerkinElmer), and a haemocytometer (FIG. 2). The data shows that rDKK2 does not influence proliferation of MC38 cells. DKK2 neutralization with its neutralizing antibodies also did not alter MC38 proliferation (not shown). Histological analysis of APC and APCKO mice for Ki67 expression, a protein associated with cell proliferation, also showed no significant difference in proliferation of the tumor or normal region.

Example 2: Lack of DKK2 Increases CD8$^+$ Activation Without Significant Effects on Other Leukocyte Subpopulations or Markers To test if DKK2 expression may alter the tumor microenvironment to render proper anti-tumor immune response, the levels and anti-tumor activity of tumor infiltrating lymphocytes (TILs) were analyzed. Due to the nature of their tumors, APC mice provide a unique opportunity to study the tumor region and compare it to the adjacent normal. The analysis including measuring the levels, activation marker and cytokine production of CD4 (IL-2, IFNg, TNFa, CD25, CD69, FoxP3), cells as well as some suppressive properties of MDSCs (Arginase and iNOS function) showed no difference in APC vs. APCKO mice. Other organs such as Peyer's patches (PPs), spleen, Mesenteric lymph nodes (MLN), lamina propria, thymus, and bone marrow were also analyzed and no significant differences were observed.

Figures 3A, 3B:
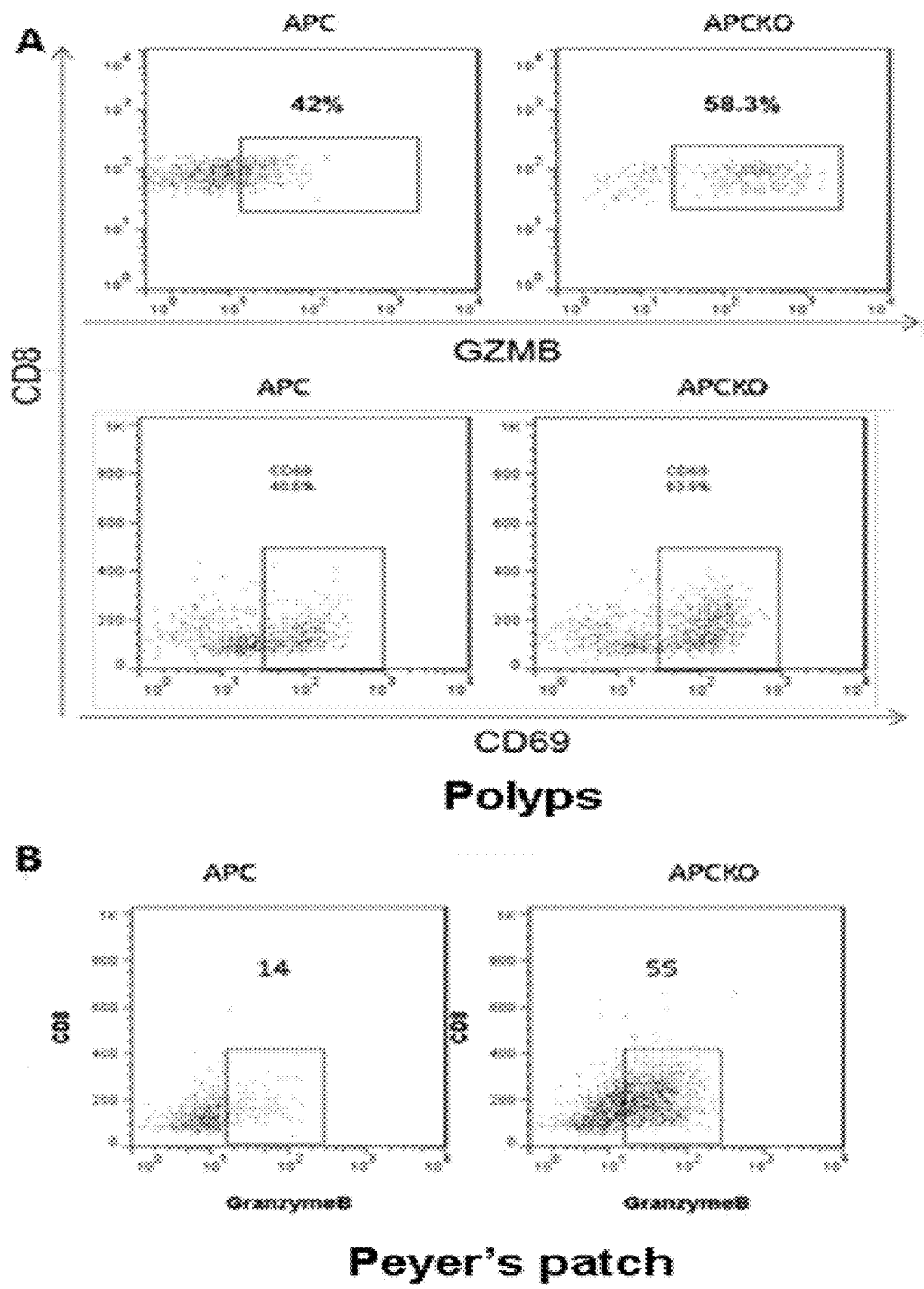
FIGS. 3A-3B are graphs depicting the flow cytometric analysis of CTLs from polyps (FIG. 3A) and Peyer's Patches (PPs) (FIG. 3B) of 18 weeks old APC or APCKO mice. CD69 and Granzyme B (GZMB) are CTL (cytotoxic T lymphocyte) activation markers. This analysis highlights that DKK2 inactivation leads to hyperactivation of CD8+ CTLs in polyps and PPs. PPs are gut lymph nodes
Figure 4:
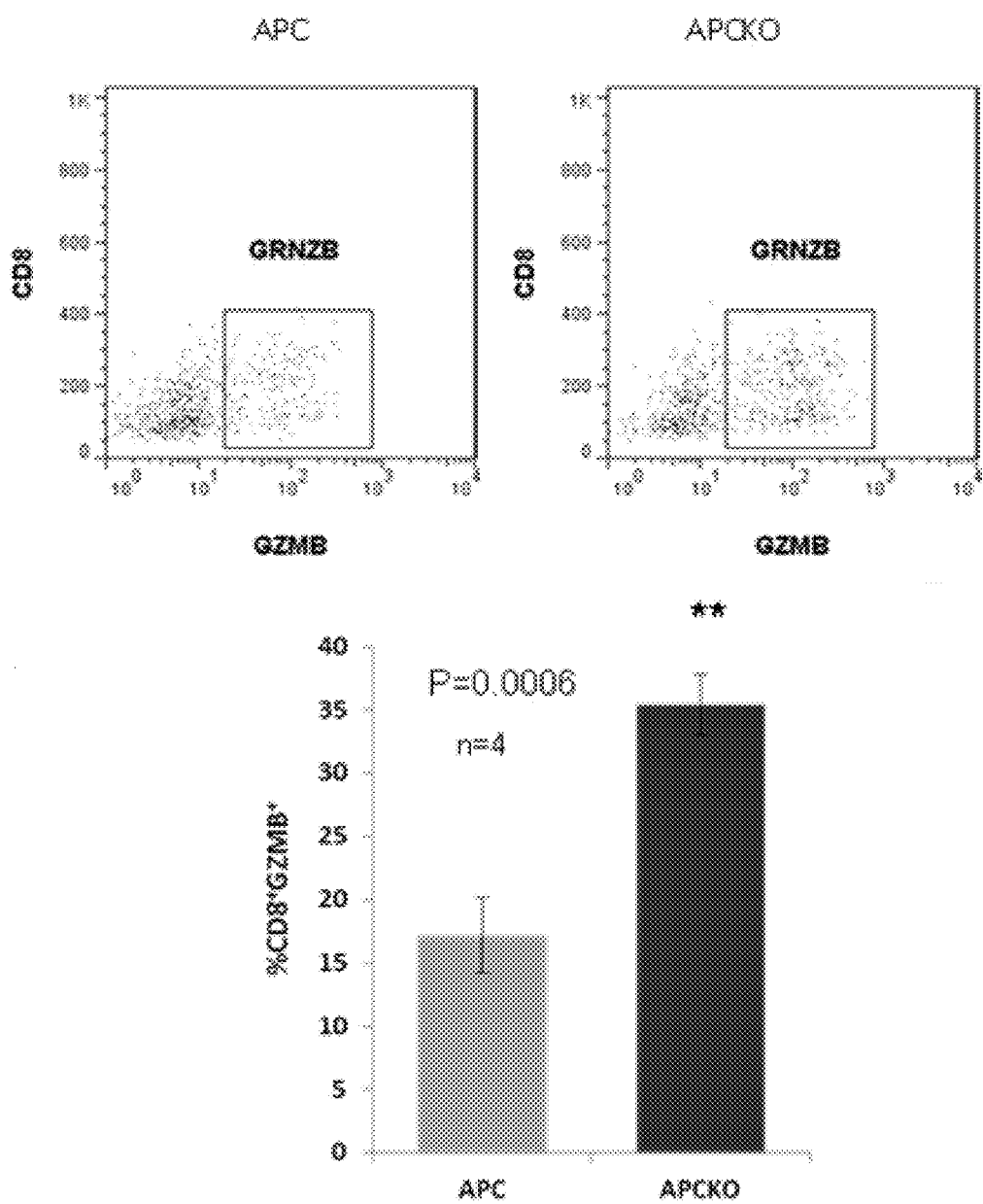
FIG. 4 is a series of graphs and histograms illustrating the increased granzyme B (gzmb) expression by CD8 cells from Peyer's patches of APCKO mice at 11 weeks, at which polyps are barely visible. APC and APKCKO are cage/litter-mates.

One of the main anti-tumor activities of the immune system includes cytotoxic activity of tumor reactive CD8$^+$ T-cells (Waldner et al., World J Gastroenterol, 2006. 12(45): p. 7233-8). CTLs through recognition of their cognate antigen within MHC I, target tumor cells and release cytotoxic compounds such as gzmb (Naito, Y., et al. Cancer Res, 1998. 58(16): p. 3491-4). Uptake of gzmb which is a serine protease leads to proteolytic activation of Caspases, cleavage of Bid, fragmentation of DNA, and induction of apoptosis in the target cells (Thornberry et al., J Biol Chem, 1997. 272(29): p. 17907-11; Heusel et al., Cell, 1994. 76(6): p. 977-87). The analysis of the TILs in APC and APCKO mice revealed a significant increase in the percentage of gzmb$^+$ and CD69+ (another CD8+ activation marker) CD8 cells (FIG. 3A). Several subtypes of CD8$^+$ T-cells infiltrate intestinal tumors; CD8ab$^+$ cells were found to have the most pronounced difference in gzmb expression (data not shown). Increased gzmb expression in CD8 TILs of APCKO coincides with higher levels of apoptotic cells in their tumors as detected in a TUNEL assay (FIG. 5). Further analysis of the lymphatic system of APC mice revealed a significantly higher level of gzmb expression in the CD8$^+$ cells of PPs in 18 week old (FIG. 3B). 11 week old mice, at which polyps are barely visible, were also analyzed for CD8$^+$ activation in their PPs. Significant increases in gzmb expression in PPs from APCKO over those from APC were observed (FIG. 4). Several other lymphatic organs were also analyzed for gzmb expression (i.e. MLN, Spleen, and inguinal LN), but no difference was observed.

Figure 6A:
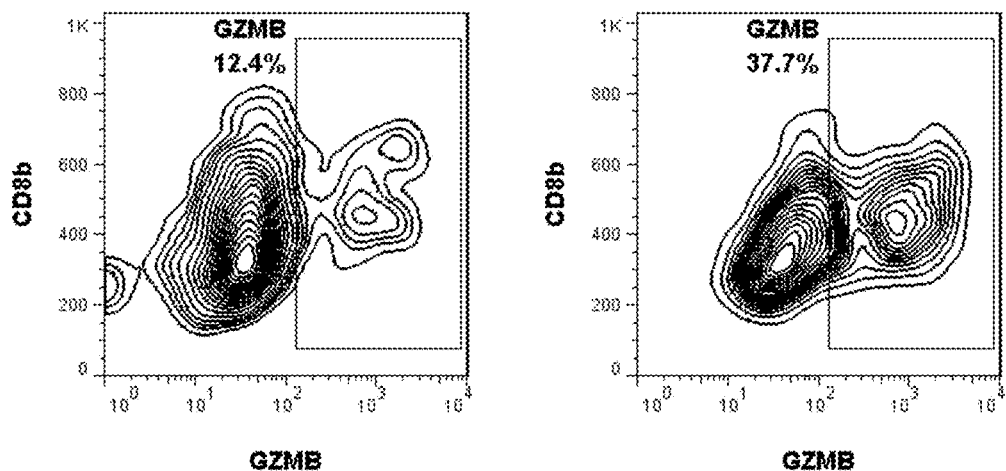
FIGS. 6A and 6B are graphs illustrating that DKK2 produced by non-hematopoietic cells largely contributes to the increases in GZMB expression on CD8 cells. Cage-mate WT and KO (DKK2$^{-/-}$) (FIG. 6A) and APC and APCKO (FIG. 6B) mice were lethally irradiated and transplanted with WT CD45.1 bone marrow cells. The mice were treated with sulfatrim for 4 weeks. 8 weeks post irradiation, they were euthanized and their PPs was harvested and analyzed for GZMB expression using flowcytometry. Increased GZMB expression on transplanted CD8 cells were observed in DKK KO mice regardless of the APC status.
Figure 6B:
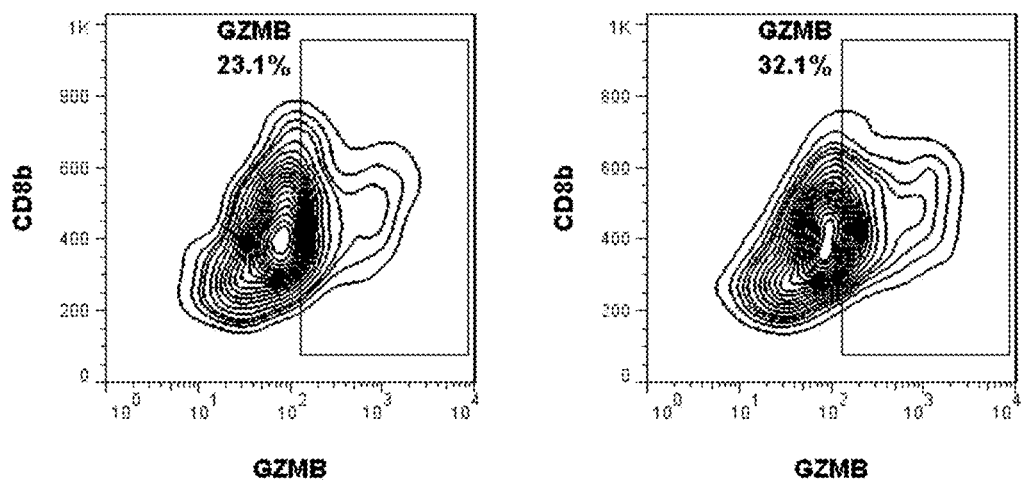
Figure 7:
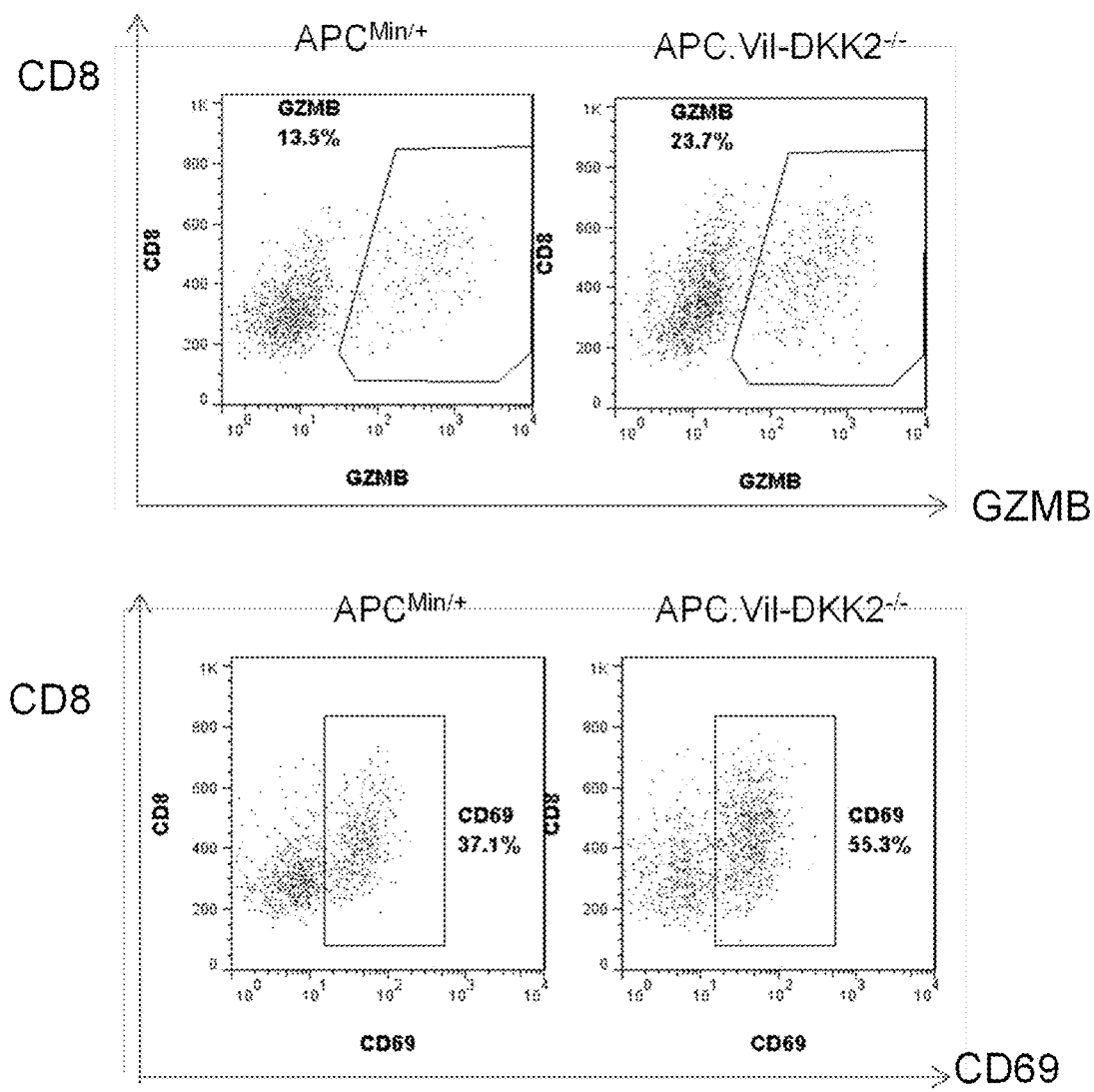
FIG. 7 is a series of graphs demonstrating that the deletion of DKK2 in epithelial cells results in increased activation of CD8 cells from Peyer's patches (PPs) of the APC mice. Cage and littermates were treated with tamoxifen at 5 weeks of age. 11 week old mice were studied for the CD8 cells. Increased gzmb and CD69 expression is detected in PPs of samples from the APC mice lacking DKK2 in epithelial cells.

Example 3: Intestinal, Non-hematopoietic DKK2 is Primarily Responsible for the Phenotype in KO Mice It was previously reported that DKK2 is expressed in the intestinal epithelial cells (Li et al., Proc Natl Acad Sci USA, 2012. 109(28): p. 11402-7). To determine whether the expression of DKK2 in the intestinal epithelial cells rather than in the immune/hematopoietic cells might be a leading cause of reduced CD8+ activity from PPs, the two following experiments were performed:
A) Generation of intestine-specific, conditional DKK2.KO mice: DKK2-floxed mice were generated and crossed them with tamoxifen inducible villin-cre mice bred to APC mice (offspring designated: APC-V-KO and APC). Indeed increased gzmb and CD69 expression was detected on tamoxifen treated 11 weeks old APC-V-KO compared to APC mice in PPs CD8 cells (FIG. 7).
B) BM adoptive transfer: To rule out the possibility that DKK2 expression in immune cells regulates the activity of CD8$^+$ T-cells, WT/KO mice were irradiated and BM adoptive transfer from CD45.1$^+$ mice was performed. Increased levels of gzmb expression in the CD45.1$^+$CD8$^+$ cells of PPs of APCKO mice (FIG. 6) were consistent with the possibility that the source of DKK2 is non-hematopoietic.

Example 4: Targeting DKK2 in Intestinal/colon Cancer has Therapeutic Benefits

Figures 8A, 8B:
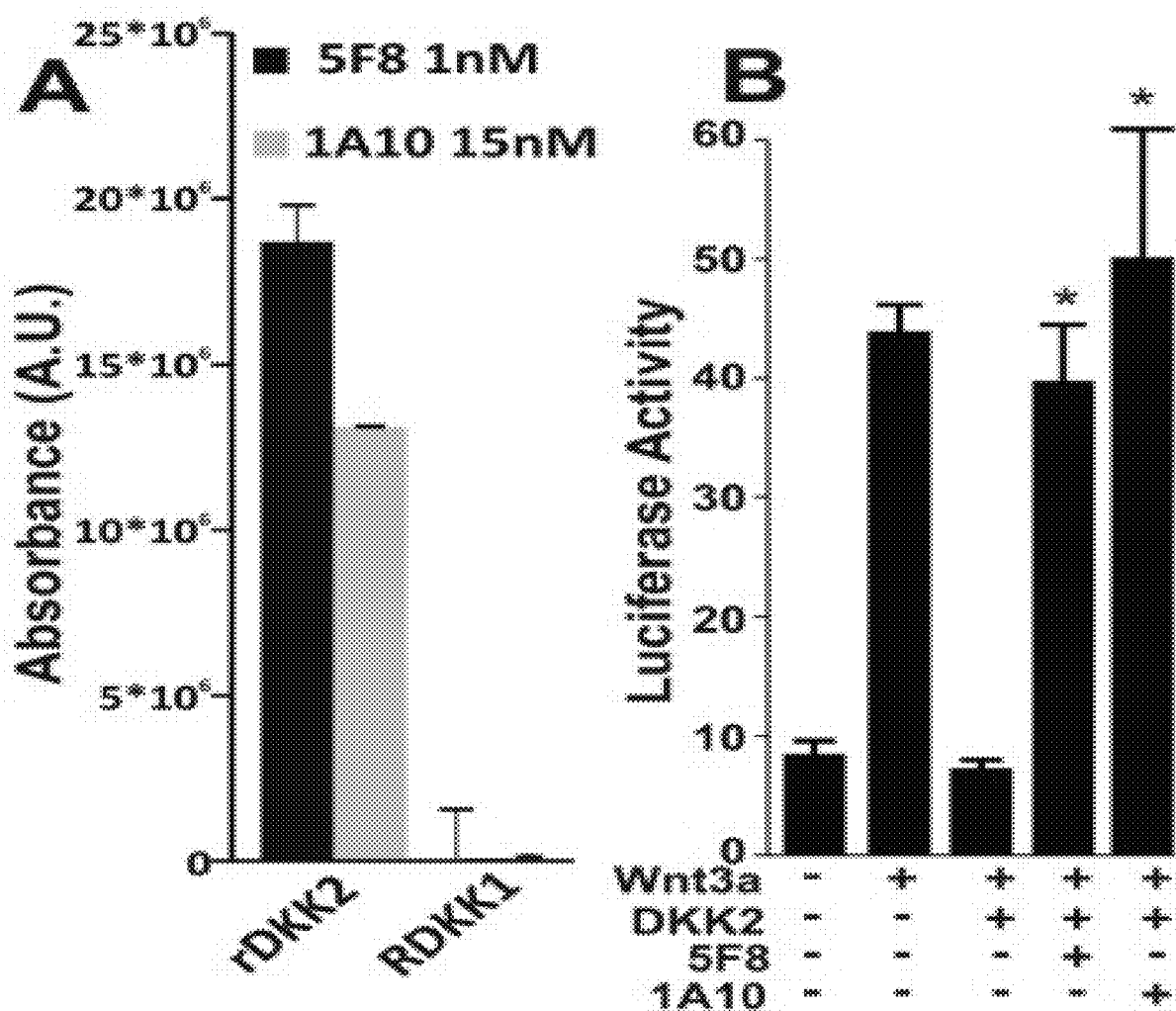
FIGS. 8A-8B are series of histograms illustrating two clones of DKK2 Antibodies YAL008-1-5F8 (5F8) and YAL008-5-1A10 (1A10).
Figures 9A, 9B, 9C:
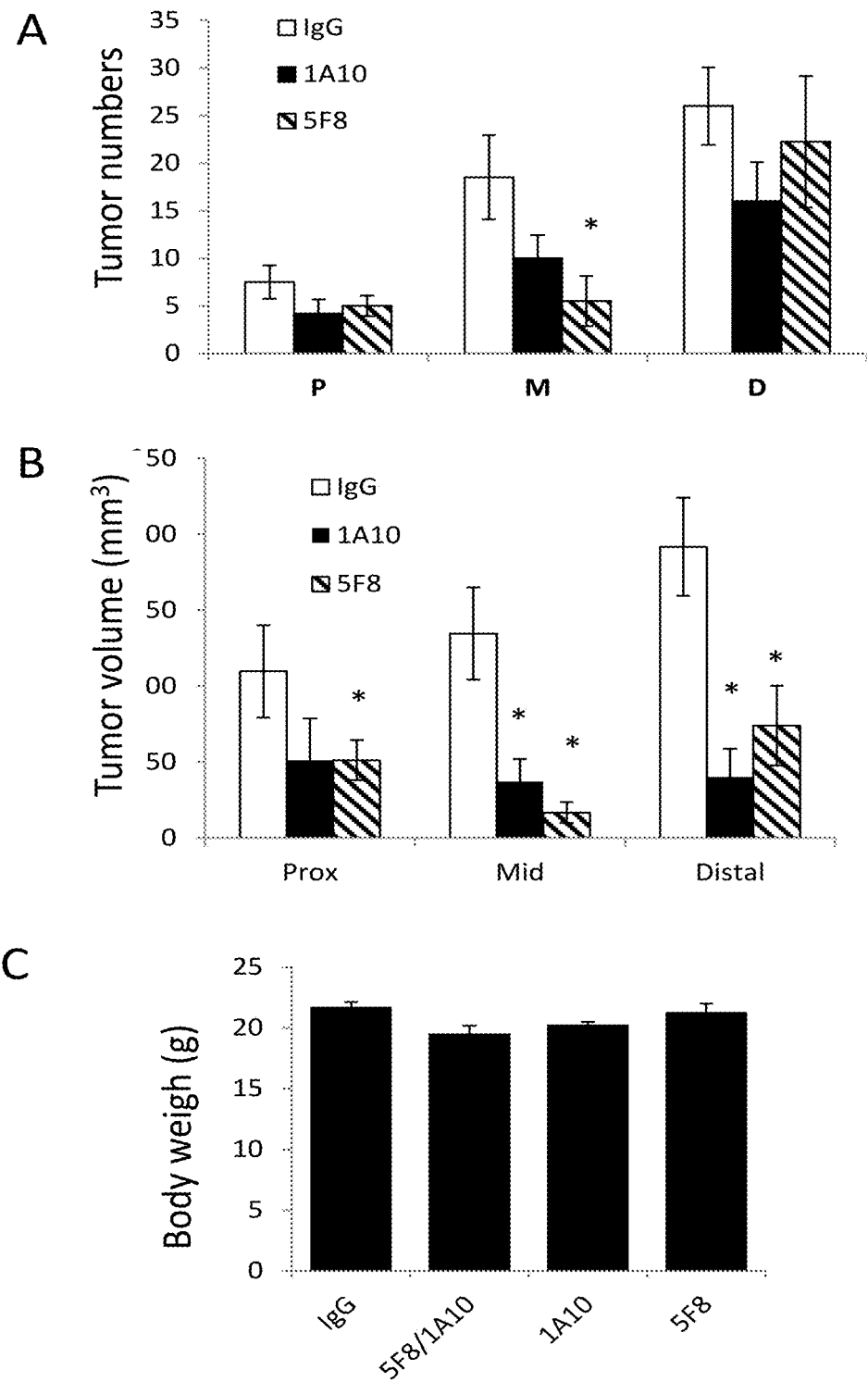
FIGS. 9A-9C illustrate DKK2 neutralization via novel a-DKK2 Ab (5F8=YAL008-1-5F8 and 1A10=YAL008-5-1A10) results in a significant reduction in tumor burden of APCmin mice. 8 week old APC mice were treated with 200 ug 5F8, 1A10, and IgG for 8 weeks every 72 hrs. Tumor burden was measured via methylene blue staining of the formalin fixed intestine. Both tumor number (FIG. 9A) and tumor volume (FIG. 9B) are lower in a-Dkk2 ab (antibody, ab) treated mice. There is no significant different in body weight (FIG. 9C). n=5, *P<0.05.
Figure 10:
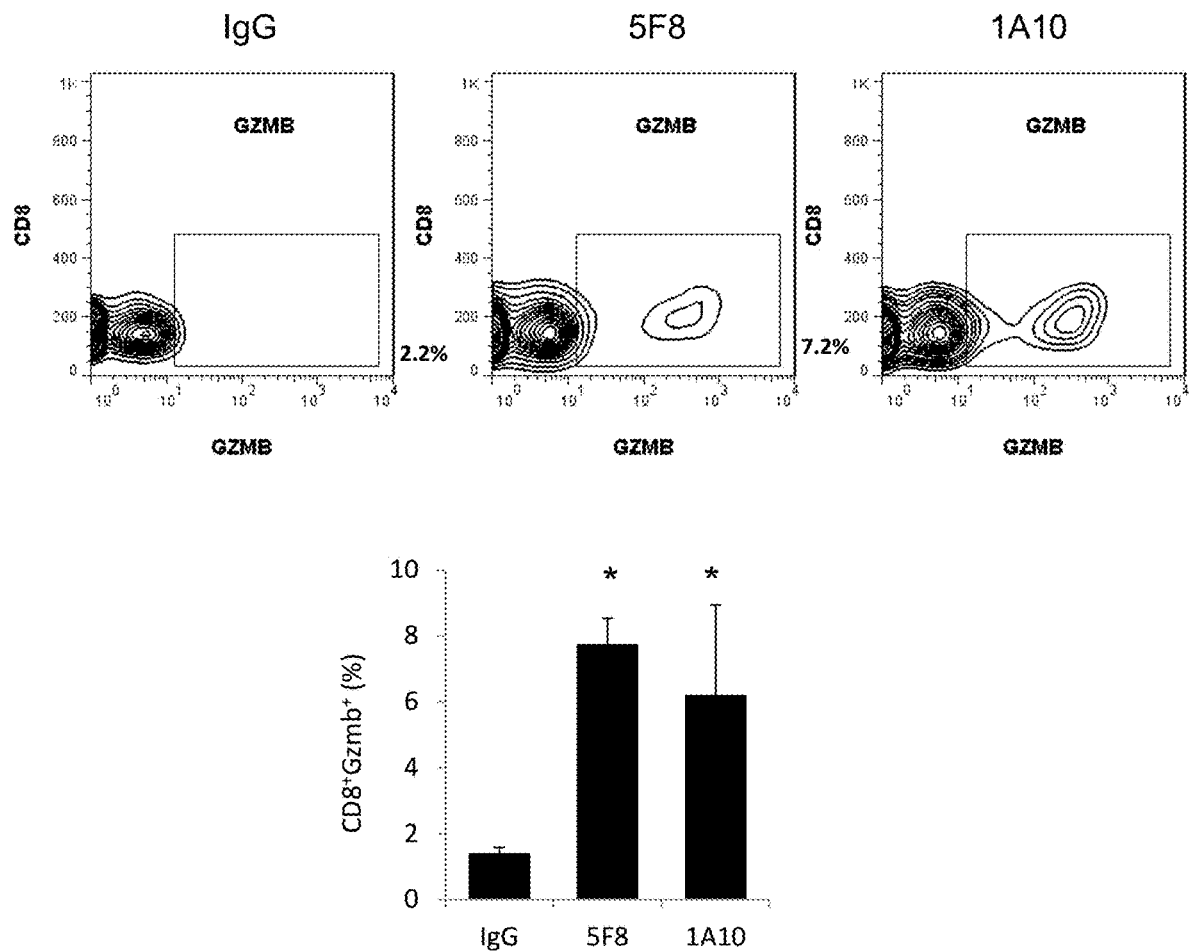
FIG. 10 is a series of graphs and histograms demonstrat-ing that the anti-DKK2 antibody increases CTL activation in Peyer's patches (PPs). n=5, *P<0.05

DKK2 is secreted and is a suitable candidate to be targeted with antibody (Ab) to reduce tumor burden. While DKK2 is important for eyelid development (Gage et al., Dev Biol, 2008. 317(1): p. 310-24), it is not known to have a vital function in adult mice. The present invention discloses three novel clones of Ab (YAL008-1-5F8, YAL008-5-1A10 and YAL008-7 1A10; FIG. 11) that were developed with high specificity for DKK2, but not DKK1 (FIG. 8A), which neutralize DKK2 and inhibit its Wnt antagonist functions (FIG. 8B). In a preliminary test, APC mice (8 weeks old) were injected intraperitoneally YAL008-1-5F8, YAL008-5-1A10, YAL008-7 1A10, or IgG. 8 weeks later their intestinal tumors were evaluated and a significant decreases in tumor number and volume of a-Dkk2 ab treated mice were observed along with lower tumor induced immune abnormalities (FIGS. 9A and 9B). The treatment had little effect on body weight, suggesting that it may not induce significant side effect (FIG. 9C). The results indicate a significant tumor/polyp reduction upon global DKK2 deletion in a colon cancer mouse model. This coincides with increased gzmb expression in PP CD8$^+$ cells in these mice (FIG. 10). Together, these results demonstrate that functional antibodies (Abs) were developed which can target and neutralize DKK2 and decrease tumor burden in APC mice, providing proof of principle evidence for therapeutic application of targeting DKK2. This difference in gzmb expression is a significant contributor to decreased tumor/polyp burden in the APCKO mice. Thus, the data presented herein highlights the role critical of DKK2 in the intestine/colon cancer progression.

Figure 13A:
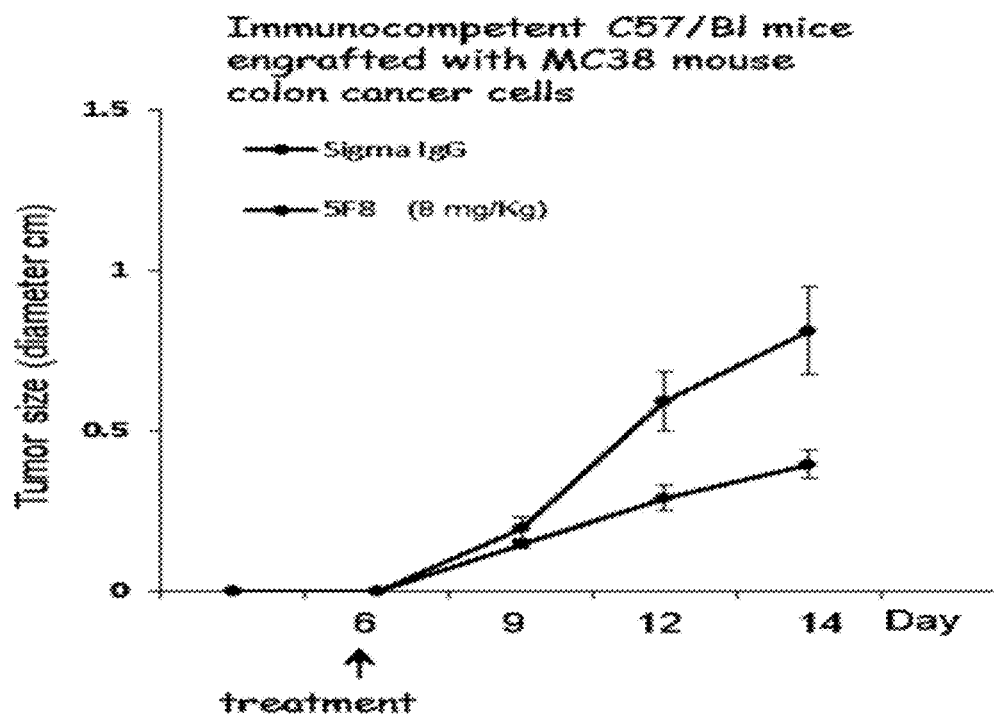
FIGS. 13A-13B are series of graphs and images showing that DKK2 neutralization reduces tumor burden accompanied by increases in Granzyme B-positive cells and tumor cell death in an allograft tumor model. Mouse colon cancer cells (MC38) were grafted subcutaneously to immunocompetent C57BL mice and treated with the anti-DKK2 antibody (5F8=YAL-008-1-5F8) starting 6 days after engraftment. Tumor growth curves (FIG. 13A) and immunostaining of tumor sections for apoptotic cells and Granzyme B positive cells (FIG. 13B) are shown. n=5
Figure 13B:
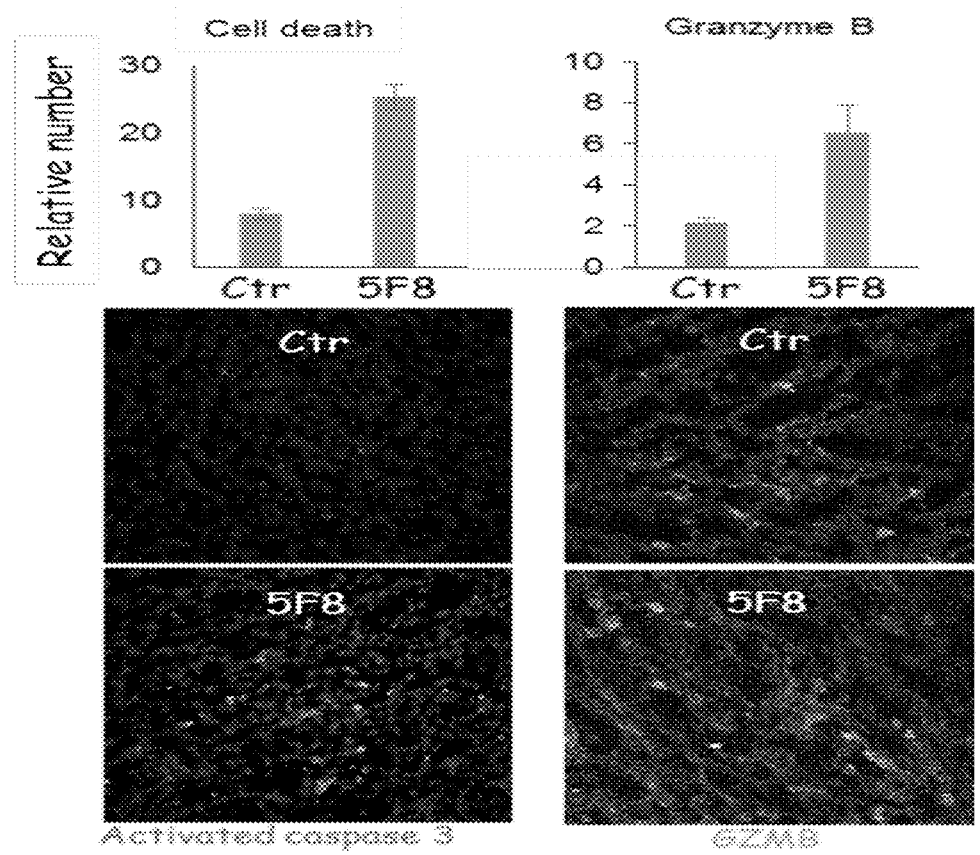
Figure 14:
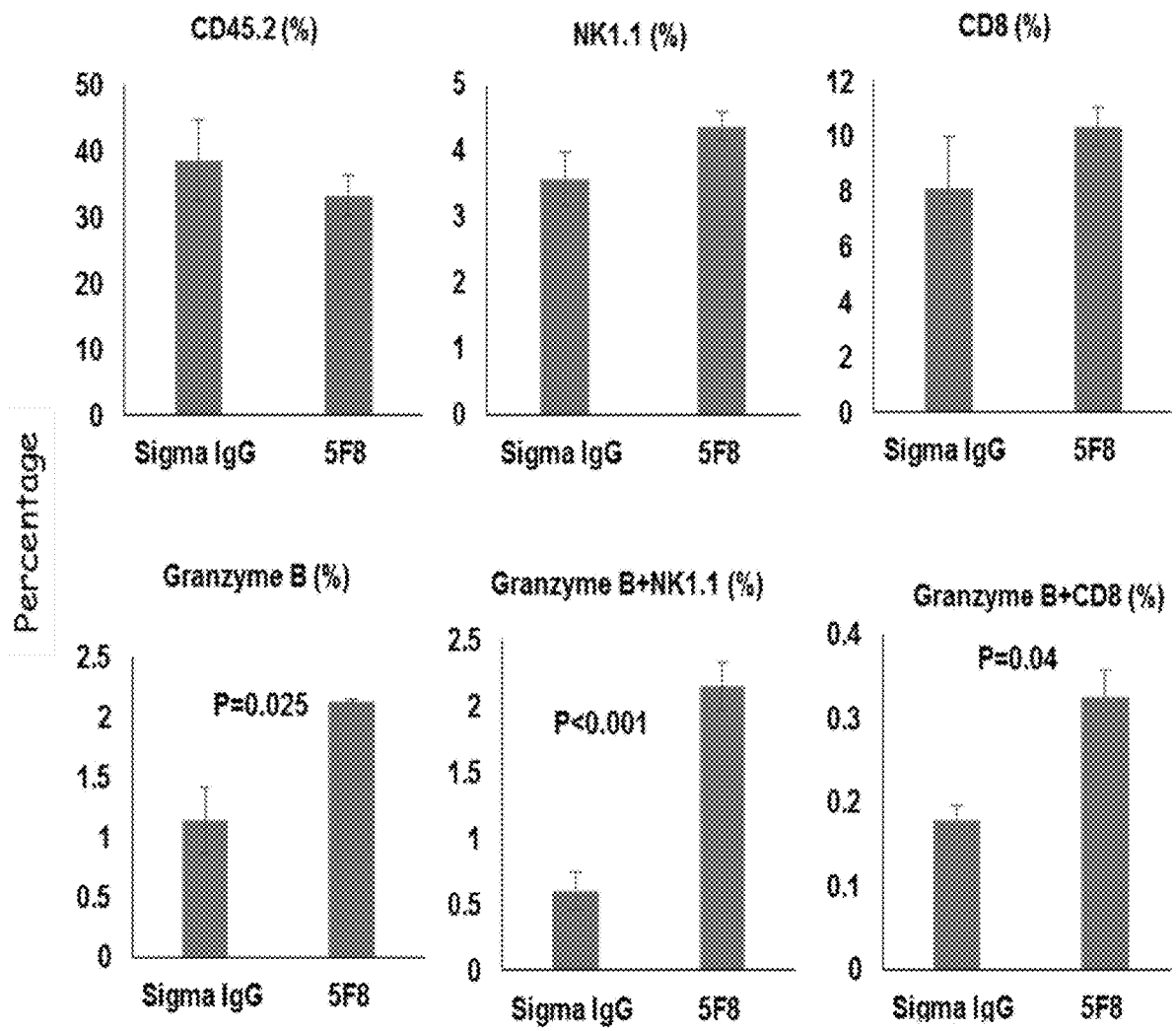
FIG. 14 is a series of histograms depicting that neutralizing anti-DKK2 antibody increases Granzyme B-positive NK and CD8 cells. Flow cytometry analysis of the cells in the allograft tumors from FIG. 13 reveals that DKK2 neutralization did not affect the number of CD45 hematopoietic cells, NK or CD8+ cells, but increase the percentage of Granzyme B positive hematopoietic cells, NK and CD8+ cells in the tumors. n=5

Example 5: Targeting DKK2 in Graft Mouse Models of Colon Cancer Cell Shows That DKK2 is An Important Player for the Regulation of Tumor Behavior and Microenvironment MC38 cells, which were derived from mouse colon carcinoma in a C57BL mouse, progress very fast when grafted to immune-competent WT C57BL mice. Thus, this Xenograft model serves as a good alternative to aggressive advanced tumor models, which can be used to test the therapeutic potential of the a-Dkk2 Abs for treating advanced cancers. In one study, C57BL mice (n=5 per group) were grafted with MC38 cells. Six days later, the mice were treated via the intraperitoneal (IP) route with mouse IgG or a-Dkk2 Ab (YAL008-1-5F8) at 8 mg/kg. FIG. 13A shows that YAL008-1-5F8 significantly inhibits tumor growth. Immunostaining of tumor sections reveals that YAL008-1-5F8 increases tumor cell apoptosis and Granzyme B-positive cells (FIG. 13B). Importantly, Flowcytometric analysis of leukocytes infiltrated into these grafted tumors shows no differences in the number of CD45, NK, CD8$^+$, myeloid cells or CD4 but YAL008-1-5F8 treatment resulted in significant increases in Granzyme B-positive CD45-positive leukocytes including Granzyme B positive NK and CD8$^+$ cells (FIG. 14). These results are consistent with genetic model study that DKK2 neutralization suppresses tumor formation via a mechanism that involves the regulation of effector immune cells.

Figure 15:
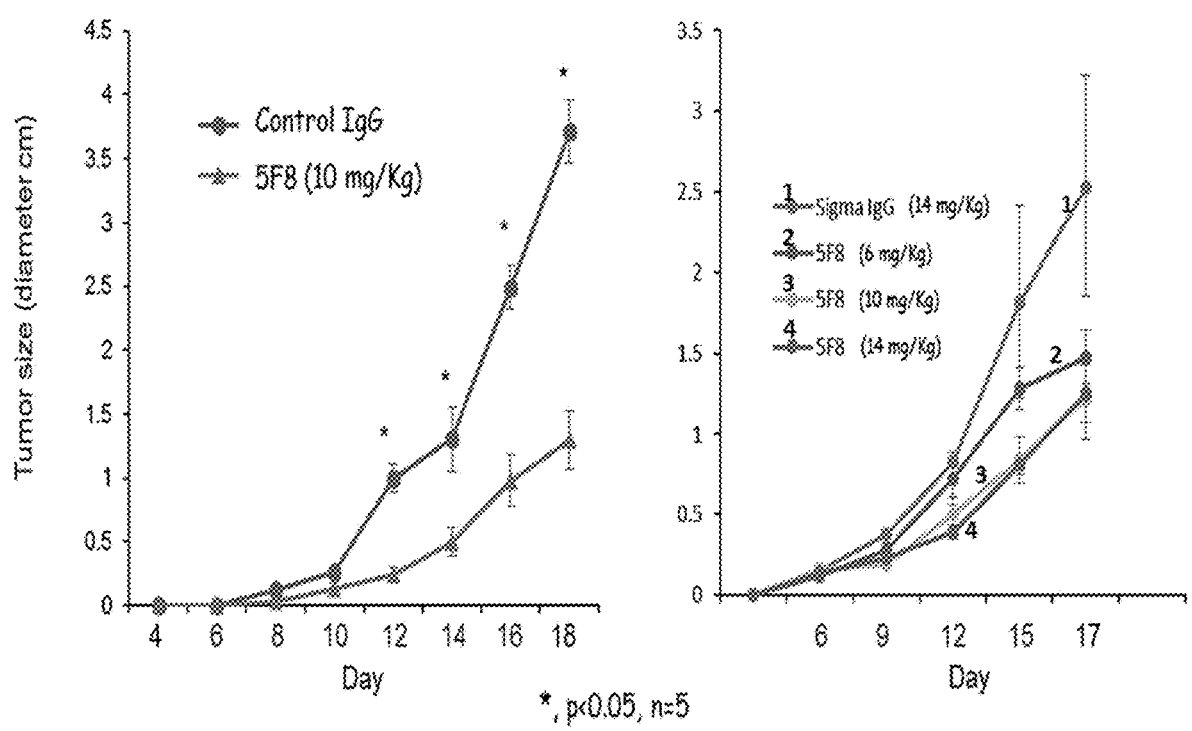
FIG. 15 is a series of graphs demonstrating that DKK2 neutralization retards tumor progression in dose-dependent manner in a longer term treatment regimen. 5F8=YAL-008-1-5F8
Figure 16:
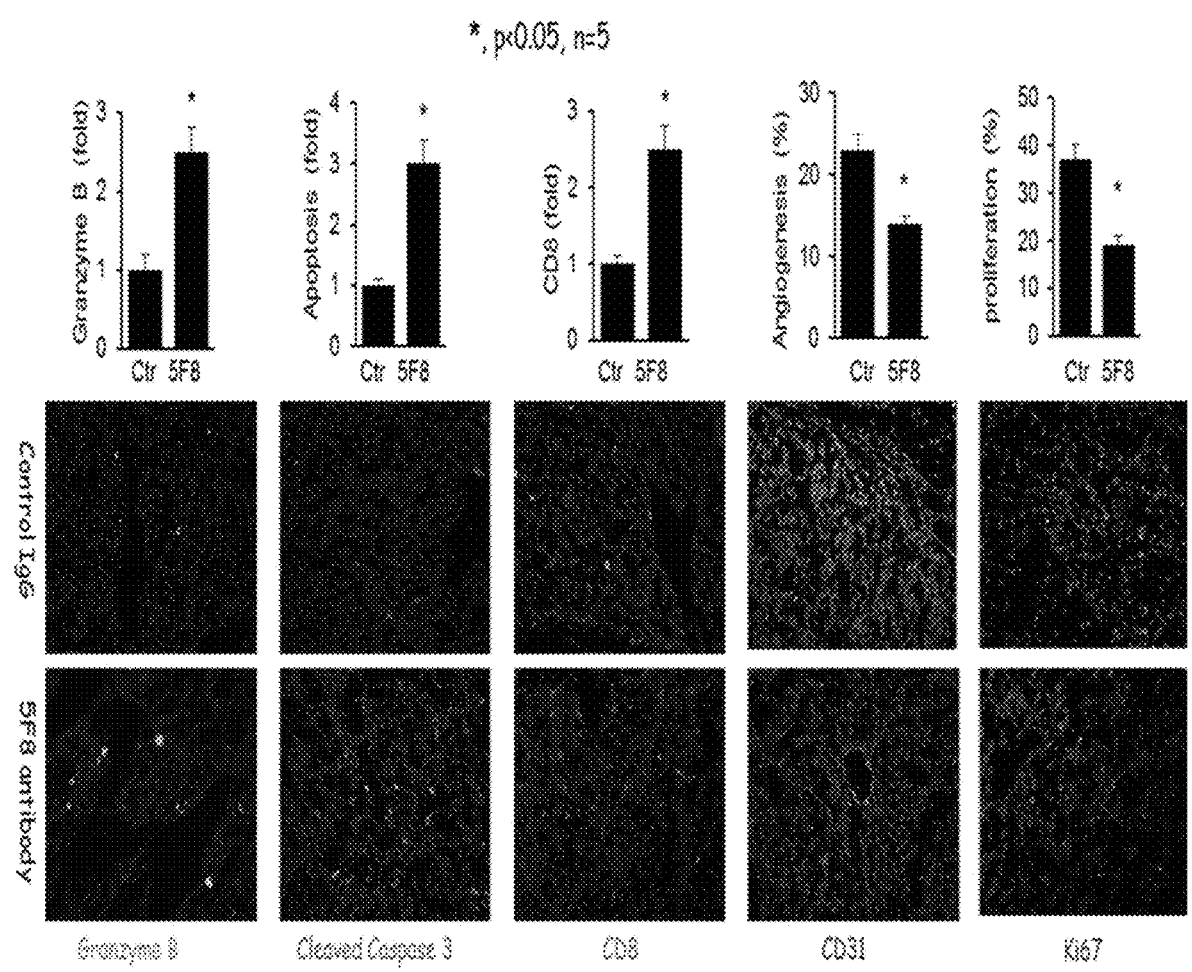
FIG. 16 is a series of histograms and images depicting that the immunostaining analysis of the tumors from FIG. 15 confirms that DKK2 neutralization increases GZMB positive cells and tumor cell death. This figure also reveals that the longer treatment of DKK2 neutralizing antibody induces secondary anti-tumor effects including an increase in CD8 cell number and decreases in tumor angiogenesis and tumor cell proliferation.

FIG. 15 shows that longer term treatment of the anti-DKK2 antibody resulted in further reduction in tumor formation in the allograft model using the MC38 cells. In addition, the antibody shows an ose-dependent effect on suppression of tumor formation. In addition to increases in Granzyme B-positive cells and tumor cell apoptosis in the tumors treated with the antibody (YAL008-1-5F8), the longer treatment leads to an increase in CD8$^+$ T cells and reduction in tumor angiogenesis and proliferation (FIG. 16).

Example 6: Targeting DKK2 in Advanced Colorectal Cancer Model

While APC mice are one of the most established mouse models, their polyps rarely transform to carcinoma. To study the targeting DKK2 in colon cancer models with stronger oncogenic mutations which develop tumors and not just polyps, several mouse strains are bred: C57BL/6APC$^{tm1Tyj/J}$ mice, B6.129S4-Kras$^{tm4Tyj/J}$ mice and villin-CreER2 mice. Tamoxifen is injected at the age of 5 weeks. 3 groups of mice (n=5) are treated with 200 ug YAL008-1-5F8/YAL008-5-1A10/IgG as of 9 weeks every 72 hrs until 18 weeks. Their intestine is fixed, the PPs are isolated for FACS analysis and tumor burden evaluation. Spleen, thymus, and blood are also collected to be analyzed for lymphopenia (B/T-cells). After tumor evaluation, the intestine is processed for histological assessment. The results should show a decreased tumor number and volume in YAL008-1-5F8 and YAL008-5-1A10 treated mice compared to IgG treated mice. Moreover, higher levels of gzmb in the CD8 cells of PPs were detected.

Example 7: Targeting DKK2 in APC Mice With Established Polyps and Tumors

Treatment is performed on 16 week old purchased APC mice (fully developed polyps/tumor) with 200 ug YAL008-1-5F8, YAL008-5-1A10 or IgG for 5 weeks every 72 hrs. On the endpoint day, the data is collected as previously described in example 7. A significant decrease in the tumor burden (number and volume) of mice treated with a-DKK2 Ab should be observed. Higher levels of gzmb in their PPs CD8 cells should also detected.

Example 8: Investigation of the Sources of DKK2 That Promotes Tumor Growth

Figure 17:
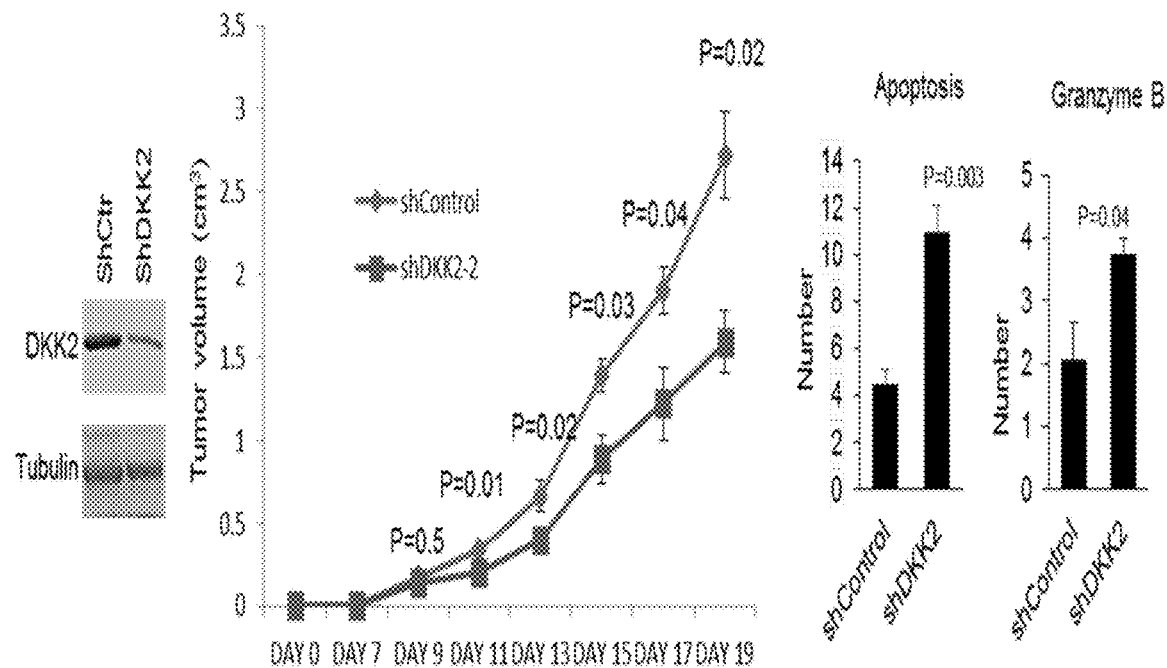
FIG. 17 is a series a graphs and histograms depicting that the reduction in DKK2 expression in tumor cells retards tumor progression accompanied by increases in GZMB-positive cells and tumor cell death. DKK2 expression in MC38 was silenced by shRNA and MC38 cells expressing lower level of DKK2 formed smaller tumors in an allograft model. Consistent with the mechanism of action eluded in the previous experiments, reduced expression of DKK2 was correlated with increases in tumor cell death and Granzyme B positive cells.

To investigate the role of tumor-produced DKK2 in tumor formation, one group of mice is injected with DKK2-shRNA-MC38 cells and the other is injected with ctrl-ShRNA-MC38 cells. The DKK2 shRNA reduces the DKK2 expression by more than one half (FIG. 17, left panel). DKK2-shRNA-MC38 cells show significant slower tumor formation in the graft model than ctrl-ShRNA-MC38 cells (FIG. 17, middle panel). Importantly, there are increases in Granzyme B-positive cells and apoptotic cells in the tumors grafted with DKK2-shRNA-MC38 cells (FIG. 17, right panel).

Figure 18:
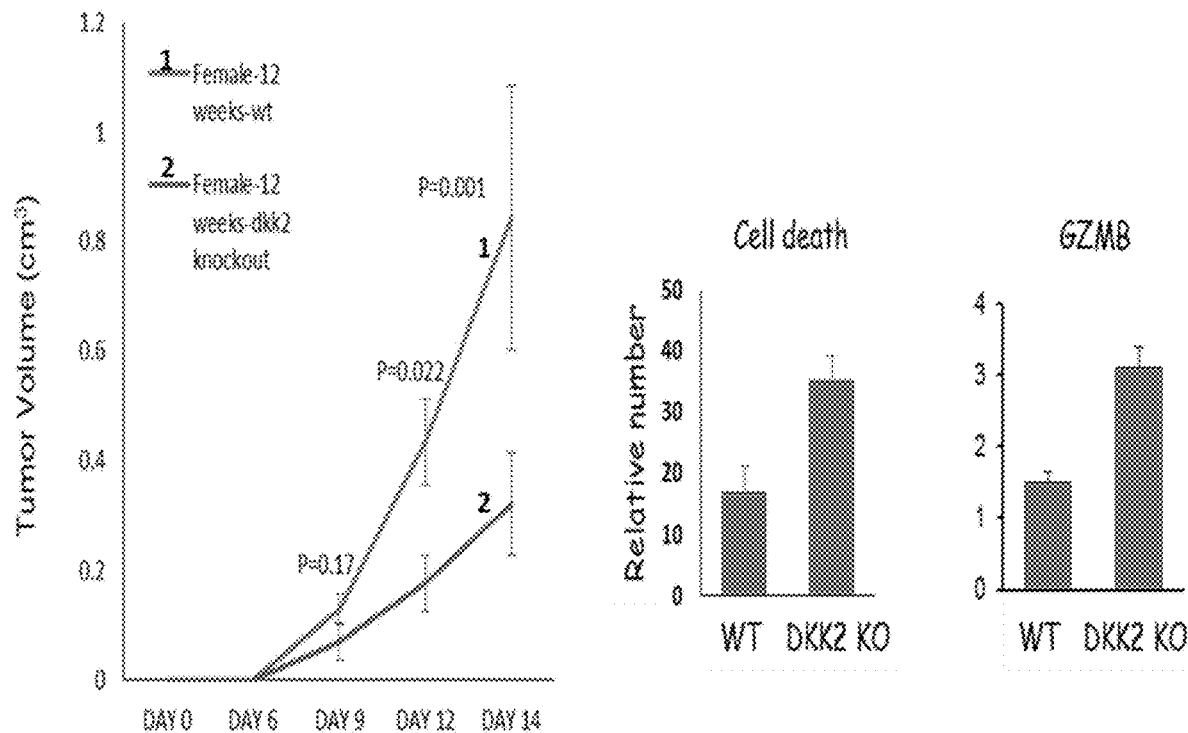
FIG. 18 is a series a graphs and histograms depicting that the inactivation of host DKK2 also retards tumor progression accompanied by increases in GZMB-positive cells and tumor cell death. Data in this figure and in FIG. 19 indicate there may be two sources of DKK2, one is the host and the other is the tumor cell. Both are important for facilitating tumor growth.

To investigate the role of DKK from the hosts, we grafted MC38 cells to WT C57BL or DKK2-null C57BL mice. FIG. 18 shows that tumors form slower on DKK2-null mice. In addition, there are increases in Granzyme B$^+$ cells and apoptotic cells in the tumors grafted on the DKK2-null mice.

Taken together, these data indicate that DKK2 produced by tumor cells and host are both important in supporting tumor growth.

Example 9: The Role of T-cells in Reduced Tumor Burden in YAL008-1-5F8 Treated APC Mice Results described herein previously have shown that a significant decrease in tumor burden in APCKO and YAL008-1-5F8 treated APC mice is accompanied by higher levels of gzmb expression in tumor of APCKO and PPs of YAL008-1-5F8 treated mice. To investigate whether T-cells are responsible for such phenomena or higher gzmb is detected because there is less tumor induced suppression T-cell lacking mice are used. Rag2 deficient mice are bred to APC mice. TB-cell knockout APC mice (n=5) are treated with YAL008-1-5F8 or IgG for 8 weeks. On the endpoint day, mice are euthanized and their tumor burden are studied. No significant difference in the tumor burden of these 2 groups should be detected. Thus, the lack of DKK2 is causing higher gzmb expression in T-cells which infiltrate intestinal tumors and kill cancer cells.

Example 10: The Role of DKK2 in Regulation of T-cell Activation

It is important to know if DKK2 is influencing gzmb expression in T-cells directly or is it influencing other cells/factors, which regulate its expression. To study this matter naïve $CD8^+$ T-cells are isolated from the spleen, MLN, iel, and PPs. These cells are incubated in CD3/CD28 coated plates with or without rDKK2 and rWnt3a in their media. After 48 and 72 hrs, corresponding respectively to early and mid-stage activation, samples are collected and analyzed for gzmb expression via FACS. An additional dose of rDKK2 is administered to wells at 48 hr since rDKK2 loses its bioactivity in long incubations. A decrease in gzmb expression should be detected once rDKK2 is added to the media supporting the idea that DKK2 is directly influencing gzmb expression.

Example 11: The Role of Intraepithelial Lymphocytes Cells (iels) in Regulation of Tumor Burden: Killing Capacity of iels in Presence and Absence of rDKK2 and YAL008-1-5F8

Increased gzmb expression in CD8 cells is strongly correlated with its cytotoxic capacity and anti-tumor properties. Several studies including the current invention have shown that iels can in fact kill colon cancer cells (Arvonen et al., Clin Exp Rheumatol, 2010, 28(1): p. 128-34; Ebert Immunology, 2009. 127(2): p. 206-15; Di Sabatino et al. Gut, 2006, 55(4): p. 469-77; Lundqvist et al., J Immunol, 1996. 157(5): p. 1926-34; Melgar et al., Immunology, 2002. 106 (4): p. 476-85 and Nussler et al., Langenbecks Arch Surg, 2000. 385(3): p. 218-24). So far, the results disclosed herein have shown that gzmb expression in $CD8^+$ Tils of APCKO was particularly elevated and the source of these cells may be the intraepithelial lymphocytes of the intestine. The phenotype of these cells is consistent with that of iels as they are highly $gzmb^+$, >95% $CD69^+$, and a significant $CD4^+$ $CD8^+$ population (a hallmark of activated $CD4^+$ iels) is observed (Pahar et al., Eur J Immunol, 2006. 36(3): p. 583-92).

To study whether DKK2 or its inhibition can directly regulate killing capacity of iels, $CD8^+$ iels from 11 week old APC mice are sorted by FACS and incubated with 10K MC38 cells in 10:1, and 5:1 E:T ratio. rDKK2 (15 nM) and YAL008-1-5F8/IgG (3 nM) are added to the media to investigate whether DKK2 can directly influence the killing capacity of iels. 24 hrs later, MC38 cells are analyzed for AnnexinV and PI staining via FACS. This experiment is repeated 3 times (n=3 each time) and should show an increased killing in YAL008-1-5F8 treated cells and decreased killing in DKK2 treated wells. This experiment is also performed on APC10.1 cells which are derived from APC mice (De Giovanni et al., Int J Cancer, 2004, 109(2): p. 200-6) and should show similar results. A gzmb inhibitor (e.g. Z-AAD-CMK (Biovision, CA) at 25-100 uM) is added to ensure the role of gzmb in cytotoxic functions of iels.

Example 12: The Role of Iels in Regulation of Tumor Burden: Killing Capacity of Iels from APC/APCKO and APC/APC-V-KO $CD8^+$ iels from 11 wk old APC/APCKO and APC/APC-V-KO mice are sorted by FACS to compare their CTL activity. Mice are age/sex matched cagemate littermates. The experiment is performed as described previously herein in example 11. A higher cytotoxic ability in iels of APCKO or APC-V-KO mice should be detected. Similar experiment with Tils CD8 of 24 week old APC/APCKO and APC/APC-V-KO mice is also performed. In this experiment intestinal tumors are carefully collected and digested before FACS sorting CD8 cells. Since tumors are very small, two mice are pooled per group. For this experiment a 5:1 E:T ratio is used.

Example 13: The Role of Wnt Signaling in Regulation of gzmb in CD8 Cells

Many studies have linked Wnt signaling to T-cell functions and Wnt signaling in memory cells is of particular note (Xue and Zhao Ann N Y Acad Sci, 2012. 1247: p. 16-33; Jeannet et al., Proc Natl Acad Sci USA, 2010. 107(21): p. 9777-82; Barker et al., Adv Cancer Res, 2000. 77: p. 1-24 and Zhou et al., Immunity, 2010. 33(2): p. 229-40). Wnt antagonistic property of DKK2 might be responsible for down-regulating gzmb. In order to investigate the role of Wnt in regulation of gzmb expression, naive thymic $CD8^+$ T-cells from LRP5/6 KO mice are sorted using beads thus selecting cells depleted of Wnt signaling. Cells are then CFSE labeled and i.v injected into 11 week old APC and APC-v-KO mice (cagemate/littermate). As previous results showed that injected naive cells which migrate to the PPs start producing gzmb 24-96 hrs post injection, PPs are collected 48 hrs later and the levels of gzmb in CFSE+ cells are measured via FACS. Since LRP5/6KO T-cells cannot respond to Wnt ligands, they should not show any difference in gzmb expression in APC/APC-v-KO mice. Thus the results presented herein should establish that the DKK2 reduction of gzmb expression in $CD8^+$ cells might be due to the inhibition of Wnt signaling.

Example 14: DKK2 for Cancer Therapy and the Use of Anti-DKK2 for Improving Cancer Immunotherapy The current invention discloses the role of DKK2 in colon cancer. The data presented herein provides strong and convincing arguments regarding the significant and unappreciated role for DKK2 in colon cancer promotion. Furthermore, as shown in this current invention, the role for DKK2 in regulation of gzmb is also highly unexpected. Thus regulating DKK2 expression in colon cancer open doors for new therapeutic options for patients. Several experiments including adoptive transfer of various knockout T-cells into APC/APCKO mice and the use of aging APC/APC-V-KO mice to study their tumor burden are ongoing. While DKK2 neutralization does not seem to stop tumor development, the fact that it might increase gzmb expression on TILs makes it an excellent tool for improving cancer vaccines or other immunotherapies which have not been 100% effective. The use of antibodies against DKK2 as presented in this invention is ideal for improving cancer immunotherapy such as improving MUC1 vaccine and PD-1 targeting in colon cancer treatment.

Figure 19:
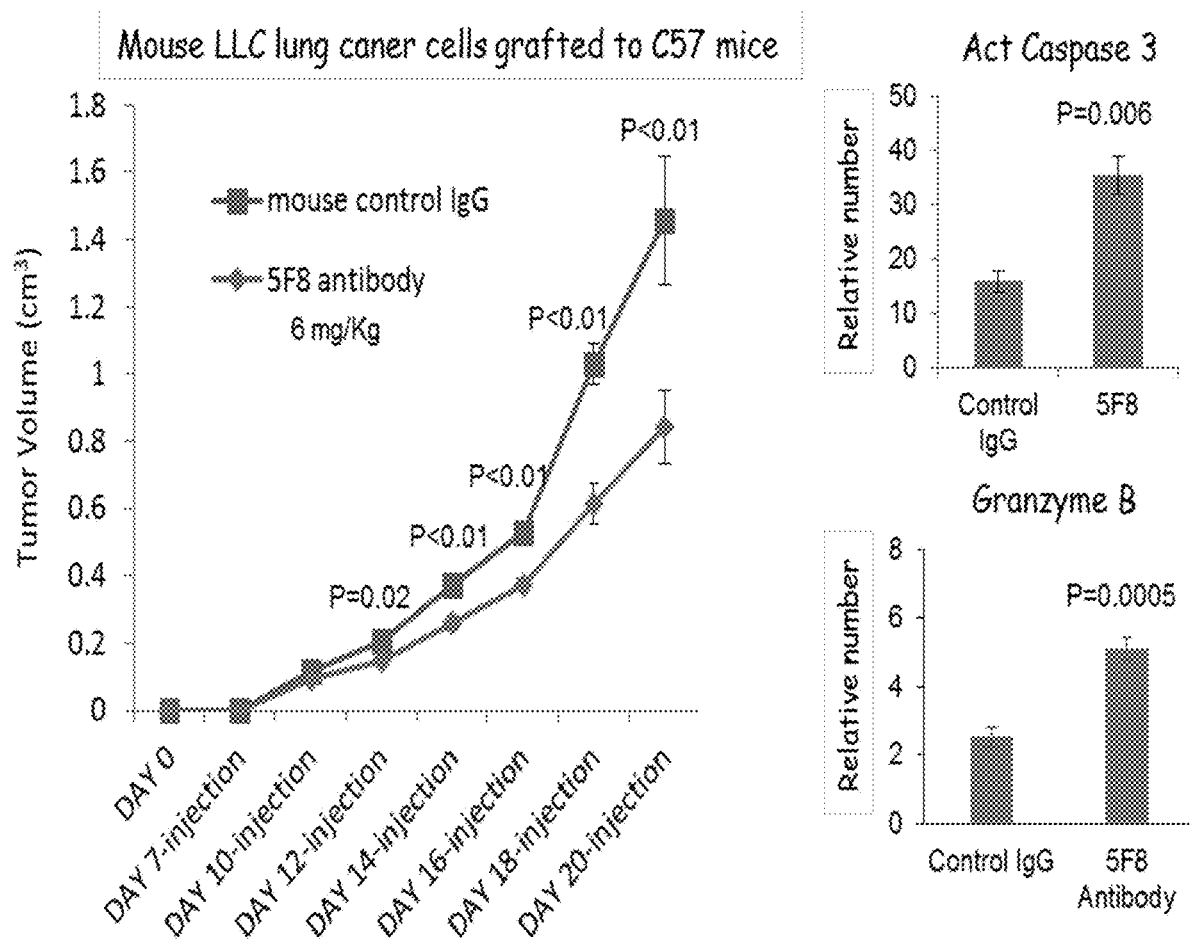
FIG. 19 is a series a graphs and histograms depicting that the DKK2 neutralization reduces lung cancer formation accompanied by increasing GZMB positive cells and tumor cell apoptosis using an allograft mouse tumor model. 5F8=YAL-008-1-5F8.

Example 15: DKK2 Antibody Suppresses Lung Tumor Formation in an Allograft Model Mouse LLC lung cancer cells were grafted to C57BL mice and treated with anti-DKK2 antibody (YAL008-1-5F8). The antibody suppressed tumor formation, accompanied by an increase in Granzyme B-positive cells and in apoptotic tumor cells (FIG. 19)

Example 16. Effect of DKK2 and Wnt on NK Cell Activation

Human NK cell line NK-92 and primary mouse NK cells from spleens and MC38-grafted tumors were tested for their expression of Granzyme and cytotoxic activity in the presence or absence of recombinant proteins of DKK2, Wnt 3a, Wnt5A and DKK1, and in the presence or absence of Wnt inhibitors (including LGK-974) and GSK inhibitors (including CHIR 99021). In this manner, regulation of NK cell activation by DKK2 and Wnt can be assessed.

Figures 20A, 20B:
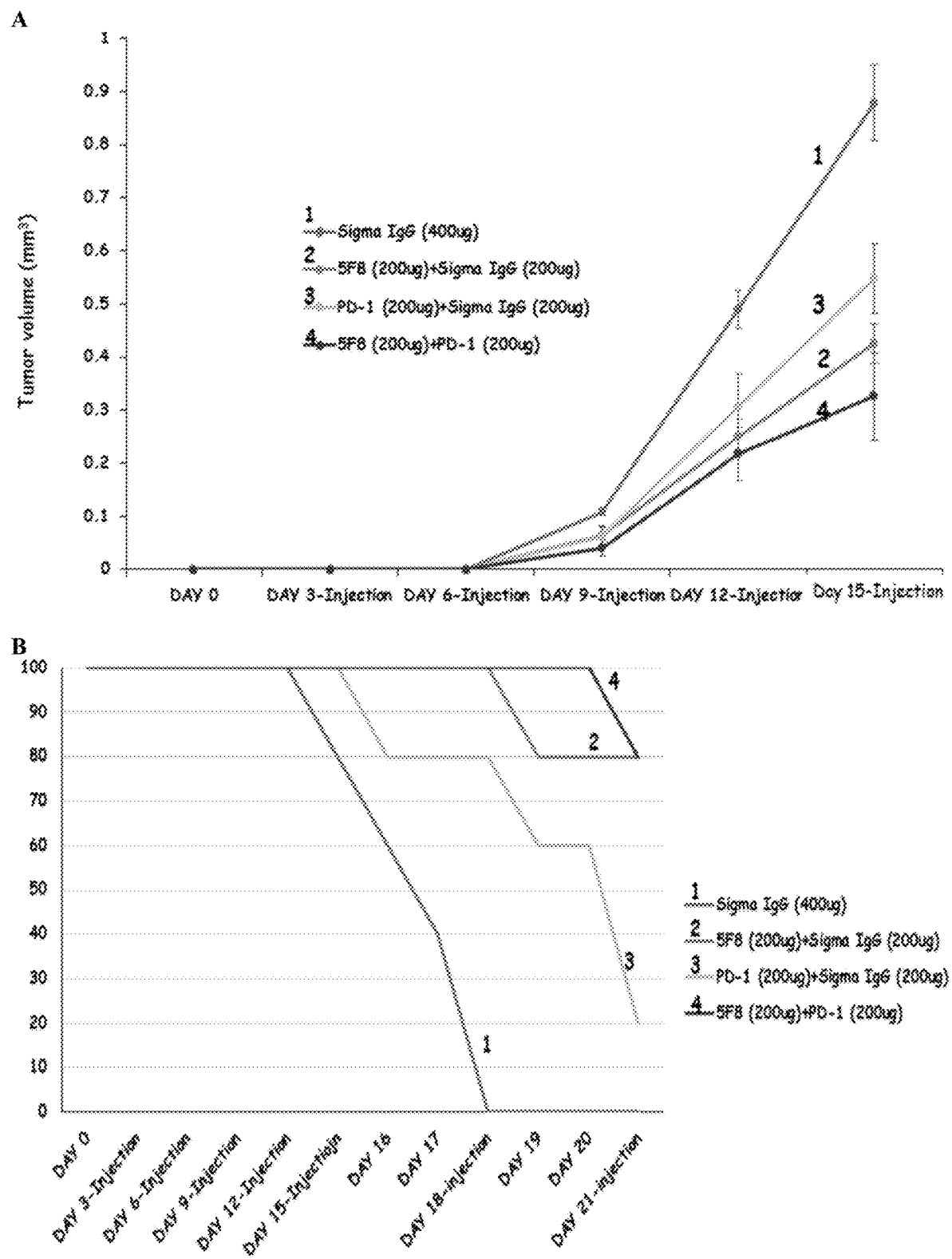
FIGS. 20A-20C are series of graphs illustrating the comparative effect of YAL-008-1-5F8 on tumors formation when administered alone or in combination with other antibodies (Sigma IgG; PD-1 antibody).
Figure 20C:
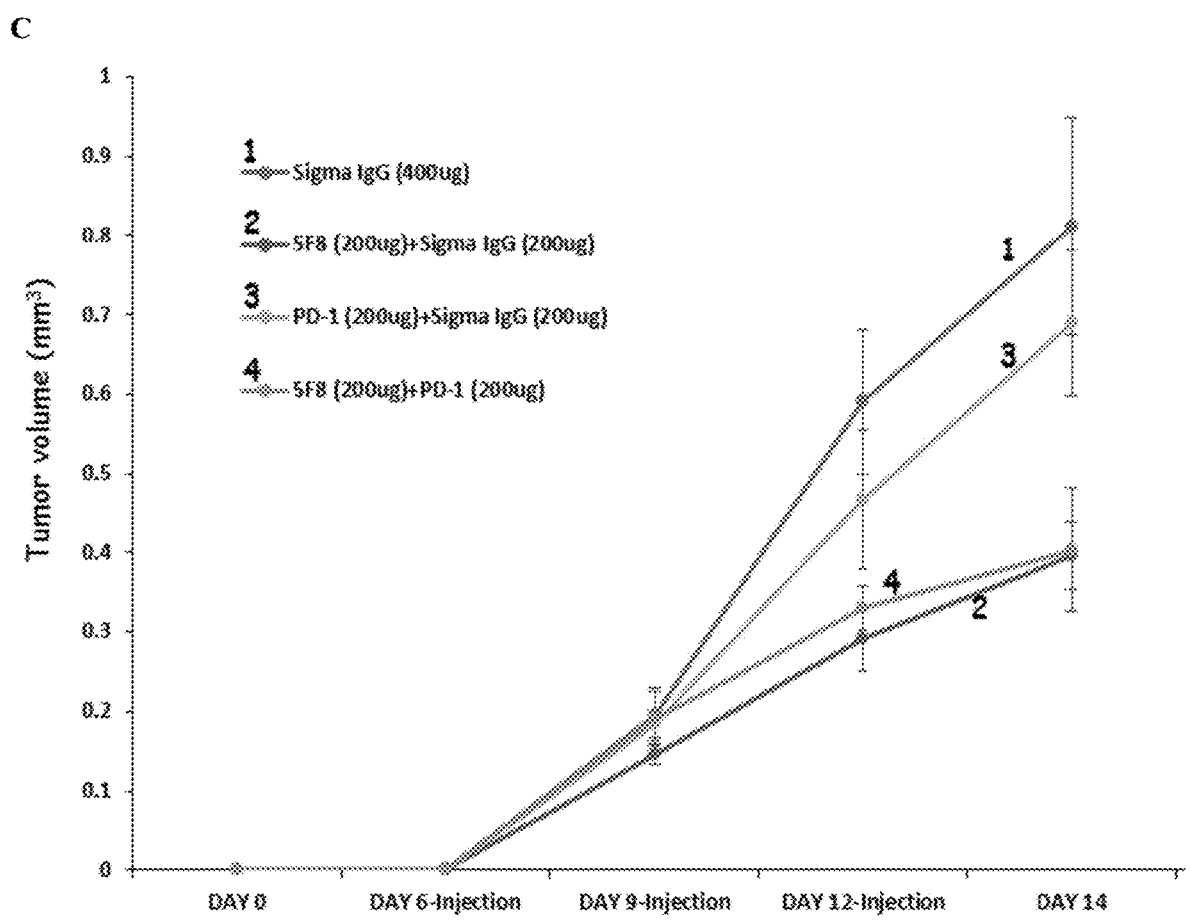

Example 17: DKK2 Antibody Optimally Suppresses Tumor Formation When Associated With PD-1 Antibody C57BL mice (n=5 per group) were grafted with LLC or MC38 cells. Six days later, the mice were treated via the intraperitoneal (IP) route with mouse IgG, a-Dkk2 Antibody (YAL008-1-5F8) and/or PD-1 antibody at 16 mg (8 mg per antibody)/kg. The effect of YAL-008-1-5F8 on tumors formation was compared with a PD-1 antibody (Cancer Res. 2005 Feb. 1; 65(3):1089-96). In the LLC allograft lung tumor model, YAL-008-1-5F8 had a similar effect on tumor retardation as did PD-1 antibody, and the combination of YAL-008-1-5F8 and PD-1 antibody exhibited a higher suppression of tumor progression than with PD-1 antibody alone (FIG. 20A); YAL-008-1-5F8 had a similar effect on mouse survival as did PD-1 antibody and the combination of YAL-008-1-5F8 and PD-1 antibody exhibited increased survival over use of PD-1 antibody alone (FIG. 20B). FIG. 20C illustrates the comparative effect of YAL-008-1-5F8 on tumor formation when administered alone or in combination with other antibodies in the MC38 colon cancer model. In this MC38 model, PD-1 antibody did not exhibit a significant effect on tumor formation.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A method of treating a cancer or a predisposition for developing a cancer in a subject, the method comprising
   detecting an increase in expression level of DKK2 in a biological sample obtained from the subject as compared with the level of DKK2 expression in a control biological sample from a subject not having a cancer, and
   treating the subject with at least one selected from the group consisting of chemotherapy, radiation therapy, immunotherapy and cancer vaccine therapy.

2. The method of claim 1, wherein the cancer is selected from the group consisting of colorectal cancer, pancreatic cancer, gastric cancer, intestinal cancer, pancreatic cancer, and esophageal cancer.

3. The method of claim 1, wherein the expression level of DKK2 in the biological sample from the subject is at least 10% greater than the normal control level.

4. The method of claim 1, wherein the expression level of DKK2 in the biological sample from the subject or normal control is determined using a method selected from the group consisting of detecting mRNA of the gene, detecting a protein encoded by the gene, and detecting a biological activity of the protein encoded by the gene.

5. The method according to claim 1, wherein the increase in the expression level of DKK2 is detected using a reagent comprising a synthetic antibody comprising at least one of the amino acid sequences selected from the group consisting of YAL008-5-1A10 (SEQ ID NOs 8 and 9), YAL008-7-1A10 (SEQ ID NOs 12 and 13) and YAL008-1-5F8 (SEQ ID NOs 10 and 11).

6. A method for determining the efficacy of a treatment for cancer in a subject in need thereof, the method comprising determining the expression level of Dickkopf2 (DKK2) gene in a biological sample obtained from the subject after treatment, wherein a decrease in the expression level of DKK2 in the biological sample from the subject as compared with the level of DKK2 expression in a control biological sample obtained from the subject before treatment is an indication that the treatment is effective, and wherein when the treatment is determined to be effective recommending additional treatment for the subject.

7. The method of claim 6, wherein the treatment comprises at least one selected from the group consisting of chemotherapy, radiation therapy, immunotherapy and cancer vaccine therapy.

8. The method of claim 6, wherein the expression level of DKK2 in the biological sample from the subject is at least 10% greater than the normal control level.

9. The method of claim 6, wherein the expression level is determined by a method selected from the group consisting of detecting mRNA of the gene, detecting a protein encoded by the gene, and detecting a biological activity of the protein encoded by the gene.

10. The method of claim 6, wherein the treatment comprises of at least a DKK2 depleting agent.

11. The method of claim 6, wherein the cancer is selected from the group consisting of colorectal cancer, gastric cancer, intestinal cancer, pancreatic cancer, and esophageal cancer.

12. The method according to claim 6, wherein the expression level of DKK2 is determined using a reagent comprising a synthetic antibody comprising at least one of the amino acid sequences selected from the group consisting of YAL008-5-1A10 (SEQ ID NOs 8 and 9), YAL008-7-1A10 (SEQ ID NOs 12 and 13) and YAL008-1-5F8 (SEQ ID NOs 10 and 11).

13. The method of claim 1 or 6, wherein the subject is a human.

* * * * *

SEQUENCE LISTING

```
<160> NUMBER OF SEQ ID NOS: 13

<210> SEQ ID NO 1
<211> LENGTH: 15
<212> TYPE: PRT
<213> ORGANISM: Homo Sapiens

<400> SEQUENCE: 1

Lys Leu Asn Ser Ile Lys Ser Ser Leu Gly Gly Glu Thr Pro Gly
1               5                   10                  15

<210> SEQ ID NO 2
<211> LENGTH: 13
<212> TYPE: PRT
<213> ORGANISM: Homo Sapiens

<400> SEQUENCE: 2

Arg Asp Arg Asn His Gly His Tyr Ser Asn His Asp Cys
1               5                   10

<210> SEQ ID NO 3
<211> LENGTH: 13
<212> TYPE: PRT
<213> ORGANISM: Homo Sapiens

<400> SEQUENCE: 3

Gly Arg Pro His Thr Lys Met Ser His Ile Lys Gly Cys
1               5                   10

<210> SEQ ID NO 4
<211> LENGTH: 13
<212> TYPE: PRT
<213> ORGANISM: Homo Sapiens
```

<400> SEQUENCE: 4

Thr Lys Gln Arg Lys Lys Gly Ser His Gly Leu Glu Cys
1               5                   10

<210> SEQ ID NO 5
<211> LENGTH: 14
<212> TYPE: PRT
<213> ORGANISM: Homo Sapiens

<400> SEQUENCE: 5

Cys Lys Val Trp Lys Asp Ala Thr Tyr Ser Ser Lys Ala Arg
1               5                   10

<210> SEQ ID NO 6
<211> LENGTH: 88
<212> TYPE: PRT
<213> ORGANISM: Homo Sapiens

<400> SEQUENCE: 6

Met Pro His Ile Lys Gly His Glu Gly Asp Pro Cys Leu Arg Ser Ser
1               5                   10                  15

Asp Cys Ile Asp Gly Phe Cys Cys Ala Arg His Phe Trp Thr Lys Ile
            20                  25                  30

Cys Lys Pro Val Leu His Gln Gly Glu Val Cys Thr Lys Gln Arg Lys
        35                  40                  45

Lys Gly Ser His Gly Leu Glu Ile Phe Gln Arg Cys Asp Cys Ala Lys
    50                  55                  60

Gly Leu Ser Cys Lys Val Trp Lys Asp Ala Thr Tyr Ser Ser Lys Ala
65                  70                  75                  80

Arg Leu His Val Cys Gln Lys Ile
                85

<210> SEQ ID NO 7
<211> LENGTH: 10
<212> TYPE: PRT
<213> ORGANISM: Homo Sapiens

<400> SEQUENCE: 7

Cys Ala Arg His Phe Trp Thr Lys Ile Cys
1               5                   10

<210> SEQ ID NO 8
<211> LENGTH: 109
<212> TYPE: PRT
<213> ORGANISM: Homo Sapiens

<400> SEQUENCE: 8

Leu Gln Gln Ser Gly Pro Glu Leu Val Lys Pro Gly Ala Ser Val Lys
1               5                   10                  15

Ile Ser Cys Lys Ala Ser Gly Tyr Ser Phe Thr Gly Tyr Phe Val Asn
            20                  25                  30

Trp Val Lys Gln Ser His Gly Lys Ser Leu Asp Trp Ile Gly Arg Ile
        35                  40                  45

Ile Pro Tyr Asn Gly Asp Thr Phe Tyr Asn Gln Lys Phe Lys Gly Lys
    50                  55                  60

Ala Thr Leu Thr Val Asp Lys Ser Ser Thr Thr Ala His Met Glu Leu
65                  70                  75                  80

Leu Ser Leu Thr Ser Glu Asp Ser Ala Val Tyr Tyr Cys Gly Arg Gly
                85                  90                  95

Asp Tyr Trp Gly Gln Gly Thr Ser Val Thr Val Ser Ser
            100                 105

<210> SEQ ID NO 9
<211> LENGTH: 105
<212> TYPE: PRT
<213> ORGANISM: Homo Sapiens

<400> SEQUENCE: 9

Pro Leu Thr Leu Ser Val Thr Ile Gly Gln Pro Ala Ser Ile Ser Cys
1               5                   10                  15

Lys Ser Ser Gln Ser Leu Leu Asp Ser Asp Gly Lys Thr Tyr Leu Asn
            20                  25                  30

Trp Leu Leu Gln Arg Pro Gly Gln Ser Pro Lys Arg Leu Ile Tyr Leu
        35                  40                  45

Val Ser Lys Leu Asp Ser Gly Val Pro Asp Arg Phe Thr Gly Ser Gly
    50                  55                  60

Ser Gly Thr Asp Phe Thr Leu Lys Ile Ser Arg Val Glu Ala Glu Asp
65                  70                  75                  80

Leu Gly Val Tyr Tyr Cys Trp Gln Gly Thr His Phe Pro Gln Thr Phe
                85                  90                  95

Gly Gly Gly Thr Lys Leu Glu Ile Lys
            100                 105

<210> SEQ ID NO 10
<211> LENGTH: 115
<212> TYPE: PRT
<213> ORGANISM: Homo Sapiens

<400> SEQUENCE: 10

Gly Ala Glu Leu Val Arg Pro Gly Ala Ser Val Lys Leu Ser Cys Lys
1               5                   10                  15

Ala Ser Gly Tyr Ser Phe Thr Asn Tyr Trp Met Asn Trp Val Lys Gln
            20                  25                  30

Arg Pro Gly Gln Gly Leu Glu Trp Ile Gly Met Ile His Pro Ser Asp
        35                  40                  45

Ser Glu Thr Arg Leu Asn Gln Lys Phe Lys Asp Lys Ala Thr Leu Thr
    50                  55                  60

Val Asp Lys Ser Ser Ser Thr Ala Tyr Met Gln Leu Ser Ser Pro Thr
65                  70                  75                  80

Ser Glu Asp Ser Ala Val Tyr Tyr Cys Ala Arg Glu Gly Arg Leu Gly
                85                  90                  95

Leu Arg Ser Tyr Ala Met Asp Tyr Trp Gly Gln Gly Thr Ser Val Thr
            100                 105                 110

Val Ser Ser
        115

<210> SEQ ID NO 11
<211> LENGTH: 104
<212> TYPE: PRT
<213> ORGANISM: Homo Sapiens

<400> SEQUENCE: 11

Pro Ser Ser Leu Ala Met Ser Val Gly Gln Lys Val Thr Met Ser Cys
1               5                   10                  15

Lys Ser Ser Gln Ser Leu Leu Asn Ser Asn Gln Lys Asn Tyr Leu
            20                  25                  30

Ala Trp Tyr Gln Gln Lys Pro Gly Gln Ser Pro Lys Leu Leu Val Tyr
             35                  40                  45

Phe Ala Ser Thr Arg Glu Ser Gly Val Pro Asp Arg Phe Val Gly Ser
         50                  55                  60

Gly Ser Gly Thr Asp Phe Thr Leu Thr Ile Thr Ser Val Gln Ala Glu
65                  70                  75                  80

Asp Leu Ala Asp Tyr Phe Cys Gln Gln His Tyr Ile Thr Pro Leu Thr
                 85                  90                  95

Phe Gly Ala Gly Thr Lys Leu Glu
            100

<210> SEQ ID NO 12
<211> LENGTH: 102
<212> TYPE: PRT
<213> ORGANISM: Homo Sapiens

<400> SEQUENCE: 12

Ser Asn Pro Val Thr Ser Gly Glu Ser Val Ser Ile Ser Cys Arg Ser
1               5                  10                  15

Ser Lys Ser Leu Leu Tyr Lys Asp Gly Lys Thr Tyr Leu Asn Trp Phe
             20                  25                  30

Leu Gln Arg Pro Gly Gln Ser Pro Gln Leu Leu Ile Tyr Leu Met Ser
         35                  40                  45

Thr Arg Ala Ser Gly Val Ser Asp Arg Phe Ser Gly Ser Gly Ser Gly
     50                  55                  60

Thr Asp Phe Thr Leu Glu Ile Ser Arg Val Lys Ala Glu Asp Val Gly
65                  70                  75                  80

Val Tyr Tyr Cys Gln Gln Leu Val Glu Tyr Pro Tyr Thr Phe Gly Gly
                 85                  90                  95

Gly Thr Lys Leu Glu Ile
            100

<210> SEQ ID NO 13
<211> LENGTH: 111
<212> TYPE: PRT
<213> ORGANISM: Homo Sapiens

<400> SEQUENCE: 13

Ser Gly Ala Glu Leu Val Lys Pro Gly Ala Ser Val Lys Met Ser Cys
1               5                  10                  15

Lys Ala Ser Gly Tyr Thr Phe Thr Asn Tyr Trp Met His Trp Val Lys
             20                  25                  30

Gln Arg Pro Gly Gln Gly Leu Glu Trp Ile Gly Thr Ile Asp Pro Ser
         35                  40                  45

Asp Ser Tyr Thr Ser Tyr Asn Gln Lys Phe Lys Gly Lys Ala Thr Leu
     50                  55                  60

Thr Val Asp Thr Ser Ser Ser Thr Ala Tyr Met Gln Leu Ser Ser Leu
65                  70                  75                  80

Thr Ser Glu Asp Ser Ala Val Tyr Tyr Cys Thr Tyr Tyr Asp Tyr Asp
                 85                  90                  95

Trp Phe Ala Tyr Trp Gly Gln Gly Thr Thr Val Thr Val Ser Ser
            100                 105                 110